US012722017B2

(12) United States Patent
Leigh et al.

(10) Patent No.: US 12,722,017 B2
(45) Date of Patent: Sep. 1, 2026

(54) HOUSING ARRANGEMENTS FOR MAGNET ROTATION

(71) Applicant: Cochlear Limited, Macquarie University (AU)

(72) Inventors: Charles Roger Aaron Leigh, North Epping (AU); Anthony Powell, Macquarie Park (AU); Kenneth Oplinger, St. Leonards (AU)

(73) Assignee: Cochlear Limited, Macquarie University (AU)

( * ) Notice: Subject to any disclaimer, the term of this patent is extended or adjusted under 35 U.S.C. 154(b) by 275 days.

(21) Appl. No.: 18/293,598

(22) PCT Filed: Jul. 27, 2022

(86) PCT No.: PCT/IB2022/056929
§ 371 (c)(1),
(2) Date: Jan. 30, 2024

(87) PCT Pub. No.: WO2023/012599
PCT Pub. Date: Feb. 9, 2023

(65) Prior Publication Data

US 2025/0108223 A1 Apr. 3, 2025

Related U.S. Application Data

(60) Provisional application No. 63/228,307, filed on Aug. 2, 2021.

(51) Int. Cl.
*A61N 1/375* (2006.01)
*A61N 1/36* (2006.01)
(Continued)

(52) U.S. Cl.
CPC ......... *A61N 1/375* (2013.01); *A61N 1/36038* (2017.08); *H04R 25/554* (2013.01);
(Continued)

(58) Field of Classification Search
CPC ... A61N 1/375; A61N 1/36038; H04R 25/554
See application file for complete search history.

(56) References Cited

U.S. PATENT DOCUMENTS 10,674,287 B2 * 6/2020 Leigh .................. H04R 25/554
2012/0014546 A1 * 1/2012 Puria ..................... H04R 11/02
381/320

(Continued)

FOREIGN PATENT DOCUMENTS

CN 104487134 A 4/2015
CN 106178254 A 12/2016

(Continued)

OTHER PUBLICATIONS

International Search Report and Written Opinion in counterpart International Application No. PCT/IB2022/056929, mailed Nov. 11, 2022, 8 pages.

*Primary Examiner* — Alexander Talpalatski
(74) *Attorney, Agent, or Firm* — Edell, Shapiro & Finnan, LLC

(57) ABSTRACT

Presented herein are implantable housing arrangements that are configured to receive and retain an implantable magnet therein, while also facilitating both in-plane rotation and out-of-plane rotation of the implantable magnet in the presence of external magnetic, such as that applied with an MRI. That is, the housing arrangements presented herein allow a planar (e.g., conventional/standard) implantable magnet to rotate circumferentially around a central axis of the implantable magnet (in-plane rotation), as well as angularly rotate relative to the central axis (out-of-plane rotation). The in-plane rotation and out-of-plane rotation can reduce torque during an MRI because the magnet is able to rotate so as to more closely align with the applied MRI magnetic field, resulting in less pain and less risk of tissue or device damage.

29 Claims, 15 Drawing Sheets

(51) Int. Cl.
*H04R 25/00* (2006.01)
*A61N 1/08* (2006.01)

(52) U.S. Cl.
CPC ...... *H04R 25/606* (2013.01); *A61N 2001/083* (2013.01); *H04R 2460/13* (2013.01)

(56) References Cited

U.S. PATENT DOCUMENTS

2016/0361537 A1 12/2016 Leigh et al.
2019/0046797 A1 2/2019 Calixto et al.
2019/0239007 A1 8/2019 Kennes et al.
2020/0197702 A1* 6/2020 Eigentler ............... H04R 25/60
2021/0046318 A1 2/2021 Gibson et al.

FOREIGN PATENT DOCUMENTS

CN 107771095 A 3/2018
CN 110583029 A 12/2019
CN 111050843 A 4/2020
CN 112105398 A 12/2020
EP 3307383 B1 3/2020
WO 2014-008169 A1 1/2014

* cited by examiner

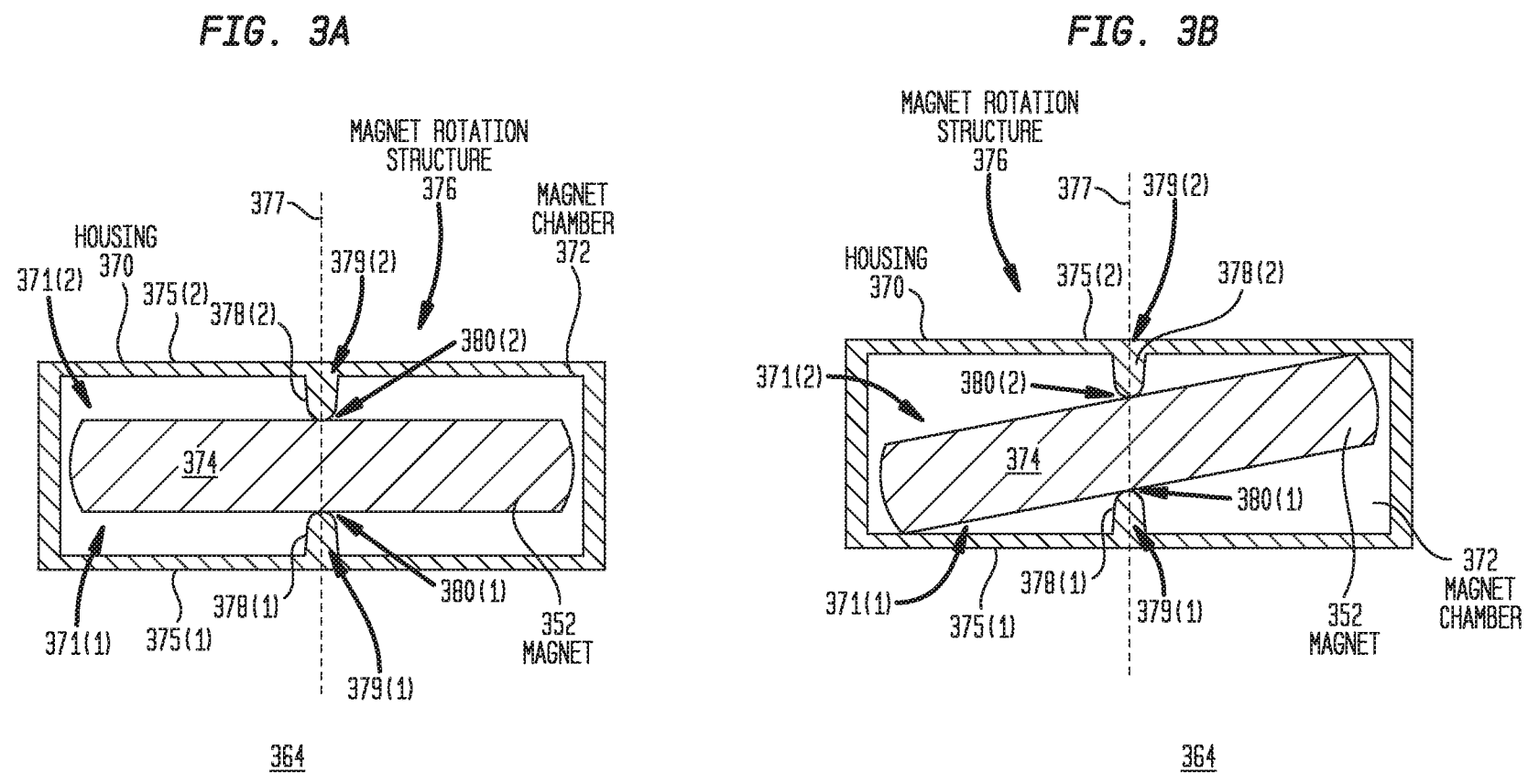

MAGNET ROTATION STRUCTURE 376
HOUSING 370
372 MAGNET CHAMBER
352 MAGNET
377
374
364
371(1) 371(2)
375(1) 375(2)
378(1) 378(2)
379(1) 379(2)
380(1) 380(2)

FIG. 3A

MAGNET ROTATION STRUCTURE 376
MAGNET CHAMBER 372
HOUSING 370
352 MAGNET
377
374
364
371(1) 371(2)
375(1) 375(2)
378(1) 378(2)
379(1) 379(2)
380(1) 380(2)

MAGNET ROTATION STRUCTURE 476
HOUSING 470
MAGNET 452
472 MAGNET CHAMBER
480
479
478
477
475(2)
474
475(1)
471(2)
471(1)
464

MAGNET
CHAMBER
572

552
MAGNET

MAGNET ROTATION
STRUCTURE
576

575(1)

577

579

580

578

575(2)

574

HOUSING
570

571(1)

571(2)

564

MAGNET ROTATION STRUCTURE 876
HOUSING 870
875(2)
HINGE 882(1)
880(2)
877
879(2)
878(2)
HINGE 882(2)
871(1)
CHAMBER MAGNET 872
874(3)
874(2)
874(1)
852(2) MAGNET
879(1)
871(2)
878(1)
880(1)
875(1)
871(1)
864

MAGNET ROTATION STRUCTURE 876
HINGE 882(2)
MAGNET CHAMBER 872
878(2)
871(1)
879(2)
877
880(2)
HINGE 882(1)
875(2)
HOUSING 870
874(3)
874(2)
874(1)
875(1)
852(3) MAGNET
879(1)
871(2)
878(1)
880(1)
852(2) MAGNET
852(1) MAGNET
864

MAGNET ROTATION STRUCTURE 876
HOUSING 870
875(2)
HINGE 882(1)
879(2)
877
878(2)
871(1)
HINGE 882(2)
874(3)
874(2)
874(1)
872 MAGNET CHAMBER
879(1)
852(2) MAGNET
882(4) HINGE
871(2)
878(1)
882(3) HINGE
875(1)
871(1)
864

MAGNET ROTATION STRUCTURE 876
MAGNET CHAMBER 872
878(2)
HINGE 882(2)
871(1)
877
879(2)
HINGE 882(1)
875(2)
HOUSING 870
874(3)
874(2)
874(1)
879(1)
852(3) MAGNET
882(4) HINGE
871(2)
852(2) MAGNET
864
878(1)
882(3) HINGE
875(1)
852(1) MAGNET

HOUSING ARRANGEMENTS FOR MAGNET ROTATION

BACKGROUND

Field of the Invention

The present invention relates generally to housing arrangements facilitating at least partial out-of-plane rotation of magnets.

Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In one aspect, an implantable medical device is provided. The implantable medical device comprises: an implantable housing defining a magnet chamber comprising a first side and a second side disposed opposite to the first side; at least one magnet disposed in the magnet chamber between the first side and the second side, wherein the at least one magnet comprises a first magnet surface adjacent the first side and a second magnet surface adjacent the second side; and a magnet rotation structure extending from at least the first side to the first magnet surface, wherein the magnet rotation structure is arranged for out-of-plane rotation of the at least one magnet in the presence of a misaligned external magnetic field.

In another aspect, an apparatus is provided. The apparatus comprises: a housing defining a magnet chamber; a magnet arrangement comprising at least a first planar magnet; and a magnet rotation structure disposed in the magnet chamber, wherein the magnet rotation structure is separate from the magnet arrangement, and wherein the magnet rotation structure is configured to permit out-of-plane rotation of the at least first planar magnet in the presence of a misaligned external magnetic field.

In another aspect, an implantable medical device system is provided. The implantable medical device system comprises: an external component comprising an external magnet; and an implantable component, comprising: a housing arrangement defining a magnet chamber, and at least one implantable magnet disposed in the magnet chamber and configured to be magnetically coupled to the external magnet, wherein the housing arrangement is configured to position the at least one implantable magnet in a first orientation when coupled to the external magnet and is configured to permit out-of-plane rotation of the at least one implantable magnet in the presence of an externally applied misaligned magnetic field.

In another aspect, a system is provided. The system comprises: a first component comprising a first magnet; and a second component, comprising: a housing arrangement including a magnet chamber, and at least one second magnet disposed in the magnet chamber and configured to be magnetically coupled to the first magnet, wherein the housing arrangement is configured to position the at least one implantable magnet in a first orientation when coupled to the first magnet and is configured to permit out-of-plane rotation of the at least one implantable magnet in the presence of a misaligned externally applied magnetic field, wherein the two opposing sides of the magnet chamber each have at least one of a conical or frustoconical shape, wherein the at least one implantable magnet is in contact with an apex of each of the two opposing sides of the magnet chamber.

In another aspect, a housing arrangement is provided. The housing arrangement comprises: a magnet chamber comprising a first side and a second side disposed opposite to the first side; a magnet rotation structure extending from at least the first side of the magnet chamber, wherein at least one magnet is disposed in the magnet chamber between the first side and the second side, and wherein the at least one magnet comprises a first magnet surface adjacent the first side and a second magnet surface adjacent the second side, and wherein the magnet rotation structure is arranged for out-of-plane rotation of the at least one magnet in the presence of a misaligned external magnetic field.

BRIEF DESCRIPTION OF THE DRAWINGS

Embodiments of the present invention are described herein in conjunction with the accompanying drawings, in which:

FIGS. 2A and 2B are cross-sectional views of an example housing arrangement, in accordance with certain embodiments presented herein;

FIGS. 3A and 3B are cross-sectional views of another example housing arrangement, in accordance with certain embodiments presented herein;

FIGS. 4A and 4B are cross-sectional views of another example housing arrangement, in accordance with certain embodiments presented herein;

FIGS. 5A and 5B are cross-sectional views of another example housing arrangement, in accordance with certain embodiments presented herein;

DETAILED DESCRIPTION

Figure 1A:
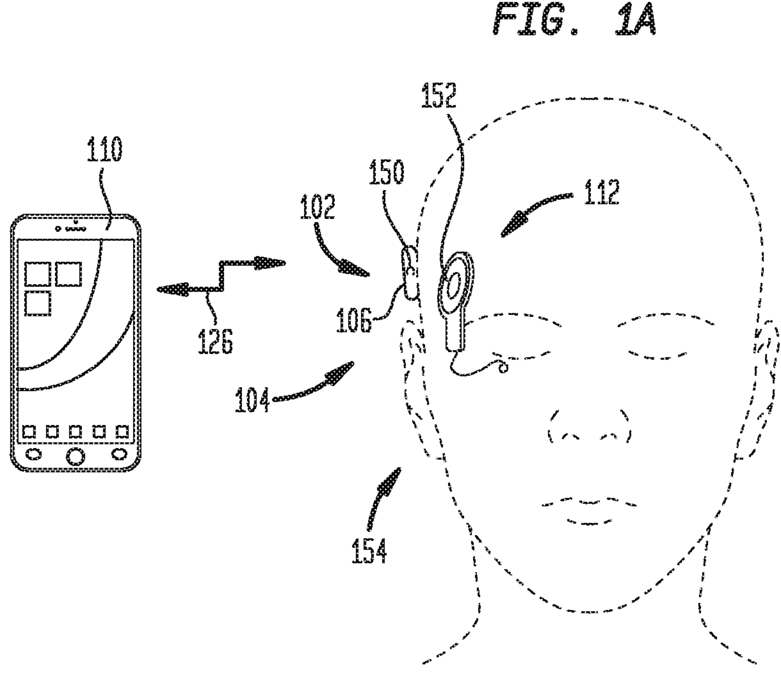
FIG. 1A is a schematic diagram illustrating a cochlear implant system with which aspects of the techniques presented herein can be implemented.

A number of different implantable medical device systems include implantable components, sometimes referred to as implantable medical devices that operate with an external component/device. For example, implantable medical devices often receive power from, receive data from, and/or send data to an external component thereof. In certain implantable medical device systems, a combination of external and internal/implantable magnets are used to properly align/position the external component with respect to the implantable medical device, which usually has a fixed position within the recipient. Such alignment facilitates efficient power and data communication between the external component and the implantable medical device.

The fact that an implantable magnet is implanted in the recipient (e.g., surgically positioned under the skin and/or tissue of the recipient) means that the implantable magnet cannot be easily removed when, for example, the recipient needs to undergo Magnetic Resonance Imaging (MRI). MRI involves the use of strong magnetic fields, magnetic field gradients, and radio waves to generate images of the organs in the body. These strong magnetic fields generate torque on the implantable magnets in a manner that causes the recipient discomfort/pain, cause malfunction and/or dislocation of the implantable medical device or the magnet in the device. Moreover, certain implantable medical devices are only approved for use with lower intensity magnetic fields, such as for 0.2 T, 1.0 T or 1.5 T MRI.

As such, in convention arrangements, indications and execution of MRI with implantable medical devices having implantable magnets require a number of restrictions and safety measures. In addition, the use of less intense magnetic field can lead to artefacts and/or a reduced validity of the results of MRI. In the end, possible defects/dislocation of the implantable medical device may still occur, and the quality of the MRI images is reduced.

Presented herein are techniques to make the use of implantable magnets less problematic in the event a recipient must undergo an MRI. In particular, presented herein are implantable "housing arrangements" that are configured to receive and retain an implantable magnet therein, while also facilitating both in-plane rotation and out-of-plane rotation of the implantable magnet in the presence of a misaligned external magnetic field, such as that applied with an MRI. That is, the housing arrangements presented herein allow a planar (e.g., conventional/standard) implantable magnet to rotate circumferentially around a central axis of the implantable magnet (in-plane rotation), as well as angularly rotate relative to the central axis, e.g., towards/away from the central axis (out-of-plane rotation), in the presence of a magnetic field that is not aligned with a central axis of the implantable magnet. The in-plane rotation and out-of-plane rotation can reduce torque in the presence of a misaligned external magnetic field because the magnet is able to rotate so as to more closely align with the direction of the applied magnetic field, resulting in less pain and less risk of tissue or device damage.

For ease of description, the techniques presented herein are primarily described with reference to use of housing arrangements with a specific implantable medical device system, namely a cochlear implant system. However, it is to be appreciated that the techniques presented herein may also be partially or fully implemented by other types of implantable medical devices. For example, the techniques presented herein may be implemented by other auditory prosthesis systems that include one or more other types of auditory prostheses, such as middle ear auditory prostheses, bone conduction devices, direct acoustic stimulators, electro-acoustic prostheses, auditory brain stimulators, combinations or variations thereof, etc. The techniques presented herein may also be implemented by dedicated tinnitus therapy devices and tinnitus therapy device systems. In further embodiments, the presented herein may also be implemented by, or used in conjunction with, vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation devices, etc.

Figure 1B:
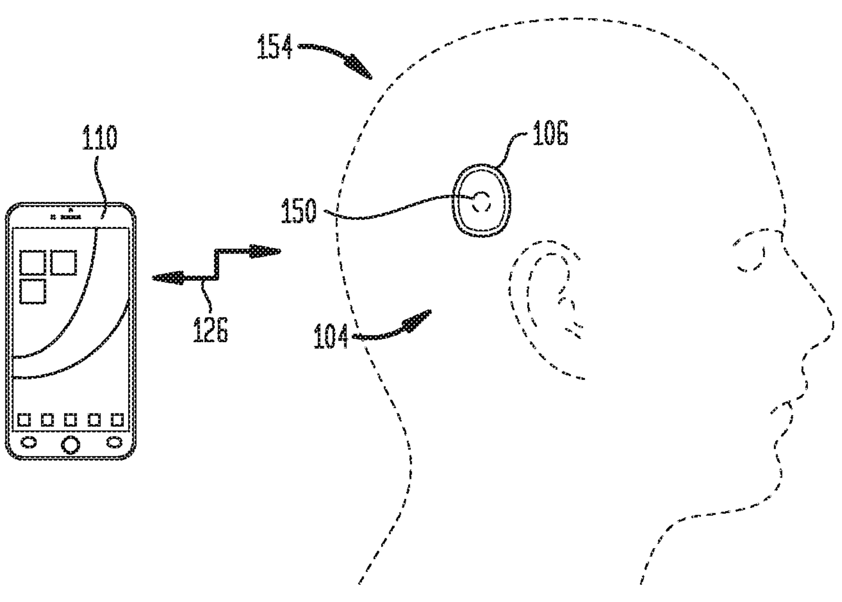
FIG. 1B is a side view of a recipient wearing a sound processing unit of the cochlear implant system of FIG. 1A.
Figure 1C:
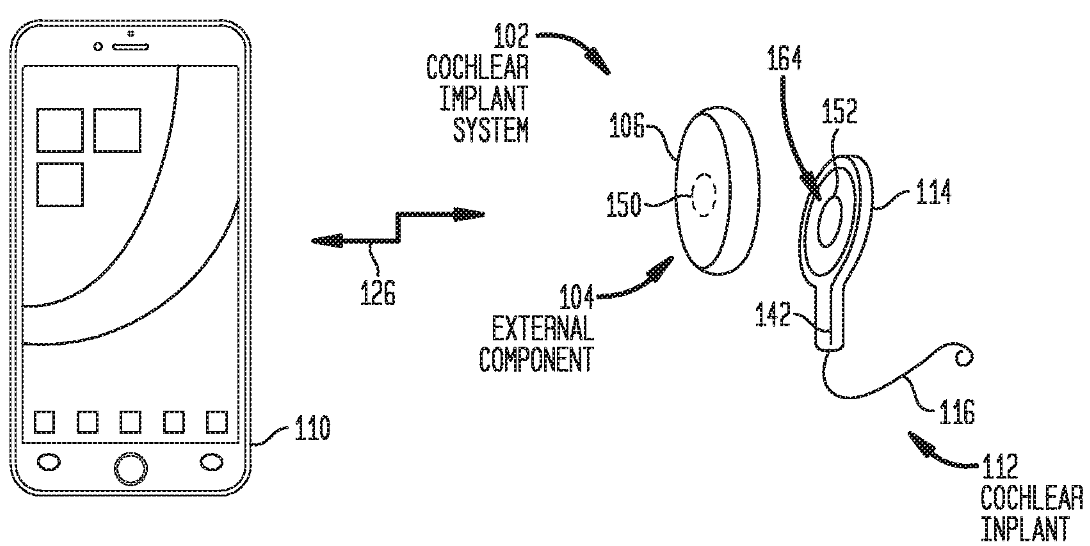
FIG. 1C is a schematic view of components of the cochlear implant system of FIG. 1A.
Figure 1D:
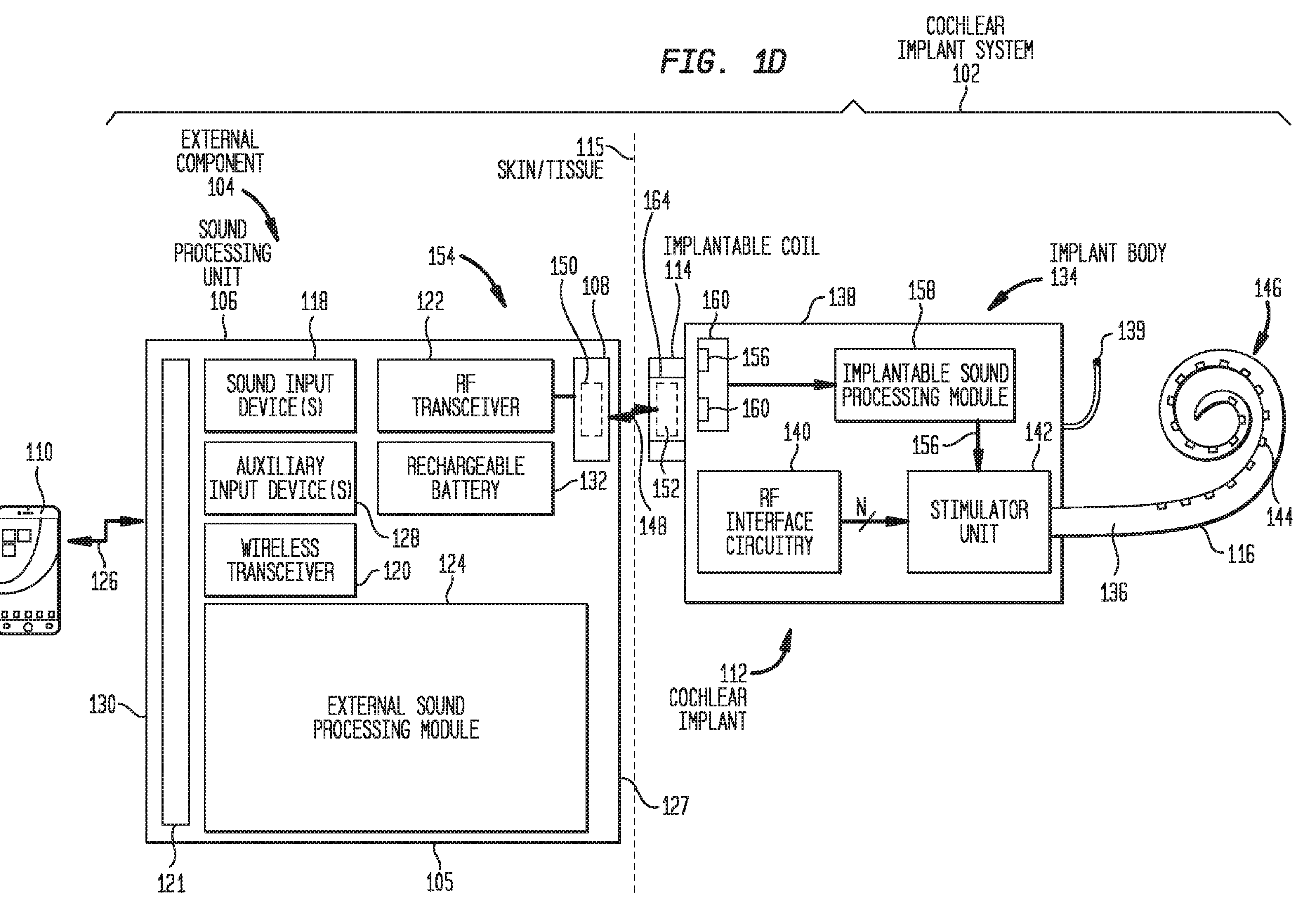
FIG. 1D is a block diagram of the cochlear implant system of FIG. 1A.

FIGS. 1A-1D illustrates an example cochlear implant system 102 with which aspects of the techniques presented herein can be implemented. The cochlear implant system 102 comprises an external component 104 and an implantable component 112 that, as described further below, includes a housing arrangement facilitating both in-plane and out-of-plane rotation of an implantable magnet. In the examples of FIGS. 1A-1D, the implantable component is sometimes referred to as a "cochlear implant" or the "implantable medical device." FIG. 1A illustrates the cochlear implant 112 implanted in the head 154 of a recipient, while FIG. 1B is a schematic drawing of the external component 104 worn on the head 154 of the recipient. FIG. 1C is another schematic view of the cochlear implant system 102, while FIG. 1D illustrates further details of the cochlear implant system 102. For ease of description, FIGS. 1A-1D will generally be described together.

Cochlear implant system 102 includes an external component 104 that is configured to be directly or indirectly attached to the body of the recipient and an implantable component 112 configured to be implanted in the recipient. In the examples of FIGS. 1A-1D, the external component 104 comprises a sound processing unit 106, while the cochlear implant 112 includes an internal coil 114, an implant body 134, and an elongate stimulating assembly 116 configured to be implanted in the recipient's cochlea.

In the example of FIGS. 1A-1D, the sound processing unit 106 is an off-the-ear (OTE) sound processing unit, sometimes referred to herein as an OTE component, that is configured to send data and power to the implantable component 112. In general, an OTE sound processing unit is a component having a generally cylindrically shaped housing and which is configured to be magnetically coupled to the recipient's head (e.g., includes an integrated external magnet 150 configured to be magnetically coupled to an implantable magnet 152 in the implantable component 112). The OTE sound processing unit 106 also includes an integrated external (headpiece) coil 108 that is configured to be inductively coupled to the implantable coil 114.

It is to be appreciated that the OTE sound processing unit 106 is merely illustrative of the external devices that could operate with implantable component 112. For example, in alternative examples, the external component may comprise a behind-the-ear (BTE) sound processing unit or a micro-BTE sound processing unit and a separate external. In general, a BTE sound processing unit comprises a housing that is shaped to be worn on the outer ear of the recipient and is connected to the separate external coil assembly via a cable, where the external coil assembly is configured to be magnetically and inductively coupled to the implantable coil 114. It is also to be appreciated that alternative external components could be located in the recipient's ear canal, worn on the body, etc.

As noted above, the cochlear implant system 102 includes the sound processing unit 106 and the cochlear implant 112. However, as described further below, the cochlear implant 112 can operate independently from the sound processing unit 106, for at least a period, to stimulate the recipient. For example, the cochlear implant 112 can operate in a first general mode, sometimes referred to as an "external hearing mode," in which the sound processing unit 106 captures sound signals which are then used as the basis for delivering stimulation signals to the recipient. The cochlear implant 112 can also operate in a second general mode, sometimes referred as an "invisible hearing" mode, in which the sound processing unit 106 is unable to provide sound signals to the cochlear implant 112 (e.g., the sound processing unit 106 is not present, the sound processing unit 106 is powered-off, the sound processing unit 106 is malfunctioning, etc.). As such, in the invisible hearing mode, the cochlear implant 112 captures sound signals itself via implantable sound sensors and then uses those sound signals as the basis for delivering stimulation signals to the recipient. Further details regarding operation of the cochlear implant 112 in the external hearing mode are provided below, followed by details regarding operation of the cochlear implant 112 in the invisible hearing mode. It is to be appreciated that reference to the external hearing mode and the invisible hearing mode is merely illustrative and that the cochlear implant 112 could also operate in alternative modes.

In FIGS. 1A and 1C, the cochlear implant system 102 is shown with an external device 110, configured to implement aspects of the techniques presented. The external device 110 is a computing device, such as a computer (e.g., laptop, desktop, tablet), a mobile phone, remote control unit, etc. As described further below, the external device 110 comprises a telephone enhancement module that, as described further below, is configured to implement aspects of the auditory rehabilitation techniques presented herein for independent telephone usage. The external device 110 and the cochlear system 102 (e.g., OTE sound processing unit 106 or the cochlear implant 112) wirelessly communicate via a bi-directional communication link 126. The bi-directional communication link 126 may comprise, for example, a short-range communication, such as Bluetooth link, Bluetooth Low Energy (BLE) link, a proprietary link, etc.

Returning to the example of FIGS. 1A-ID, the OTE sound processing unit 106 comprises one or more input devices that are configured to receive input signals (e.g., sound or data signals). The one or more input devices include one or more sound input devices 118 (e.g., one or more external microphones, audio input ports, telecoils, etc.), one or more auxiliary input devices 128 (e.g., audio ports, such as a Direct Audio Input (DAI), data ports, such as a Universal Serial Bus (USB) port, cable port, etc.), and a wireless transmitter/receiver (transceiver) 120 (e.g., for communication with the external device 110). However, it is to be appreciated that one or more input devices may include additional types of input devices and/or less input devices (e.g., the wireless short range radio transceiver 120 and/or one or more auxiliary input devices 128 could be omitted).

The OTE sound processing unit 106 also comprises the external coil 108, a charging coil 130, a closely-coupled transmitter/receiver (RF transceiver) 122, sometimes referred to as or radio-frequency (RF) transceiver 122, at least one rechargeable battery 132, and an external sound processing module 124. The external sound processing module 124 may comprise, for example, one or more processors and a memory device (memory) that includes sound processing logic. The memory device may comprise any one or more of: Non-Volatile Memory (NVM), Ferroelectric Random Access Memory (FRAM), read only memory (ROM), random access memory (RAM), magnetic disk storage media devices, optical storage media devices, flash memory devices, electrical, optical, or other physical/tangible memory storage devices. The one or more processors are, for example, microprocessors or microcontrollers that execute instructions for the sound processing logic stored in memory device.

The implantable component 112 comprises an implant body (main module) 134, a lead region 136, and the intra-cochlear stimulating assembly 116, all configured to be implanted under the skin/tissue (tissue) 115 of the recipient. The implant body 134 generally comprises a hermetically-sealed housing 138 in which RF interface circuitry 140 and a stimulator unit 142 are disposed. The implant body 134 also includes the internal/implantable coil 114 that is generally external to the housing 138, but which is connected to the transceiver 140 via a hermetic feedthrough (not shown in FIG. 1D).

As noted, stimulating assembly 116 is configured to be at least partially implanted in the recipient's cochlea. Stimulating assembly 116 includes a plurality of longitudinally spaced intra-cochlear electrical stimulating contacts (electrodes) 144 that collectively form a contact or electrode array 146 for delivery of electrical stimulation (current) to the recipient's cochlea.

Stimulating assembly 116 extends through an opening in the recipient's cochlea (e.g., cochleostomy, the round window, etc.) and has a proximal end connected to stimulator unit 142 via lead region 136 and a hermetic feedthrough (not shown in FIG. 1D). Lead region 136 includes a plurality of conductors (wires) that electrically couple the electrodes 144 to the stimulator unit 142. The implantable component 112 also includes an electrode outside of the cochlea, sometimes referred to as the extra-cochlear electrode (ECE) 139.

As noted, the cochlear implant system 102 includes the external coil 108 and the implantable coil 114. The external magnet 150 is located proximate to the external coil 108 and the implantable magnet 152 is located proximate to the implantable coil 114 (e.g., the external coil 108 is disposed circumferentially around the external magnet 150 and the implantable coil 114 is disposed circumferentially around the implantable magnet 152). As noted above, in accordance with embodiments presented herein, the implantable magnet 152 is a generally planar magnet (e.g., having two opposing and elongate planar surfaces) that is disposed in a housing arrangement 164 facilitating both in-plane and out-of-plane rotation of the implantable magnet 152.

The magnets 150 and 152 facilitate the operational alignment of the external coil 108 with the implantable coil 114. This operational alignment of the coils enables the external component 104 to transmit data and power to the implantable component 112 via a closely-coupled wireless link 148 formed between the external coil 108 with the implantable coil 114. In certain examples, the closely-coupled wireless link 148 is a radio frequency (RF) link. However, various other types of energy transfer, such as infrared (IR), electromagnetic, capacitive and inductive transfer, may be used to transfer the power and/or data from an external component to an implantable component and, as such, FIG. 1D illustrates only one example arrangement.

As noted above, sound processing unit 106 includes the external sound processing module 124. The external sound processing module 124 is configured to convert received input signals (received at one or more of the input devices) into output signals for use in stimulating a first ear of a recipient (i.e., the external sound processing module 124 is configured to perform sound processing on input signals received at the sound processing unit 106). Stated differently, the one or more processors in the external sound processing module 124 are configured to execute sound processing logic in memory to convert the received input signals into output signals that represent electrical stimulation for delivery to the recipient.

As noted, FIG. 1D illustrates an embodiment in which the external sound processing module 124 in the sound processing unit 106 generates the output signals. In an alternative embodiment, the sound processing unit 106 can send less processed information (e.g., audio data) to the implantable component 112 and the sound processing operations (e.g., conversion of sounds to output signals) can be performed by a processor within the implantable component 12.

Returning to the specific example of FIG. 1D, the output signals are provided to the RF transceiver 122, which transcutaneously transfers the output signals (e.g., in an encoded manner) to the implantable component 112 via external coil 108 and implantable coil 114. That is, the output signals are received at the RF interface circuitry 140 via implantable coil 114 and provided to the stimulator unit 142. The stimulator unit 142 is configured to utilize the output signals to generate electrical stimulation signals (e.g., current signals) for delivery to the recipient's cochlea. In this way, cochlear implant system 102 electrically stimulates the recipient's auditory nerve cells, bypassing absent or defective hair cells that normally transduce acoustic vibrations into neural activity, in a manner that causes the recipient to perceive one or more components of the received sound signals.

As detailed above, in the external hearing mode the cochlear implant 112 receives processed sound signals from the sound processing unit 106. However, in the invisible hearing mode, the cochlear implant 112 is configured to capture and process sound signals for use in electrically stimulating the recipient's auditory nerve cells. In particular, as shown in FIG. 1D, the cochlear implant 112 includes a plurality of implantable sound sensors 160 and an implantable sound processing module 158. Similar to the external sound processing module 124, the implantable sound processing module 158 may comprise, for example, one or more processors and a memory device (memory) that includes sound processing logic. The memory device may comprise any one or more of: Non-Volatile Memory (NVM), Ferroelectric Random Access Memory (FRAM), read only memory (ROM), random access memory (RAM), magnetic disk storage media devices, optical storage media devices, flash memory devices, electrical, optical, or other physical/tangible memory storage devices. The one or more processors are, for example, microprocessors or microcontrollers that execute instructions for the sound processing logic stored in memory device.

In the invisible hearing mode, the implantable sound sensors 160 are configured to detect/capture signals (e.g., acoustic sound signals, vibrations, etc.), which are provided to the implantable sound processing module 158. The implantable sound processing module 158 is configured to convert received input signals (received at one or more of the implantable sound sensors 160) into output signals for use in stimulating the first ear of a recipient (i.e., the processing module 158 is configured to perform sound processing operations). Stated differently, the one or more processors in implantable sound processing module 158 are configured to execute sound processing logic in memory to convert the received input signals into output signals 156 that are provided to the stimulator unit 142. The stimulator unit 142 is configured to utilize the output signals 156 to generate electrical stimulation signals (e.g., current signals) for delivery to the recipient's cochlea, thereby bypassing the absent or defective hair cells that normally transduce acoustic vibrations into neural activity.

It is to be appreciated that the above description of the so-called external hearing mode and the so-called invisible hearing mode are merely illustrative and that the cochlear implant system 102 could operate differently in different embodiments. For example, in one alternative implementation of the external hearing mode, the cochlear implant 112 could use signals captured by the sound input devices 118 and the implantable sound sensors 160 in generating stimulation signals for delivery to the recipient.

As noted above, presented herein are implantable medical device that include "housing arrangements." As used herein, a "housing arrangement" comprises a magnet chamber/cavity in which a planar implantable magnet is positioned/retained, and a rotational structure/formation extending from one or more sides of the cavity. The rotational structure extends from the one or more sides of the cavity and only contacts the implantable magnet at a central region of one or more planar surfaces of the implantable magnet. The rotational structure operates to retain the implantable magnet therein, while facilitating both in-plane rotation and out-of-plane rotation of the implantable magnet in the presence of a misaligned external magnetic field, such as that applied with an MRI. That is, the housing arrangements presented herein allow a planar (e.g., conventional/standard) implantable magnet to rotate circumferentially around a central axis of the implantable magnet (in-plane rotation), as well as rotate towards/away from the central axis (out-of-plane rotation). FIGS. 2A-2B, 3A-3B, 4A-4B, and 5A-5C illustrate example housing arrangements in accordance with various embodiments presented herein.

Figures 2A, 2B:
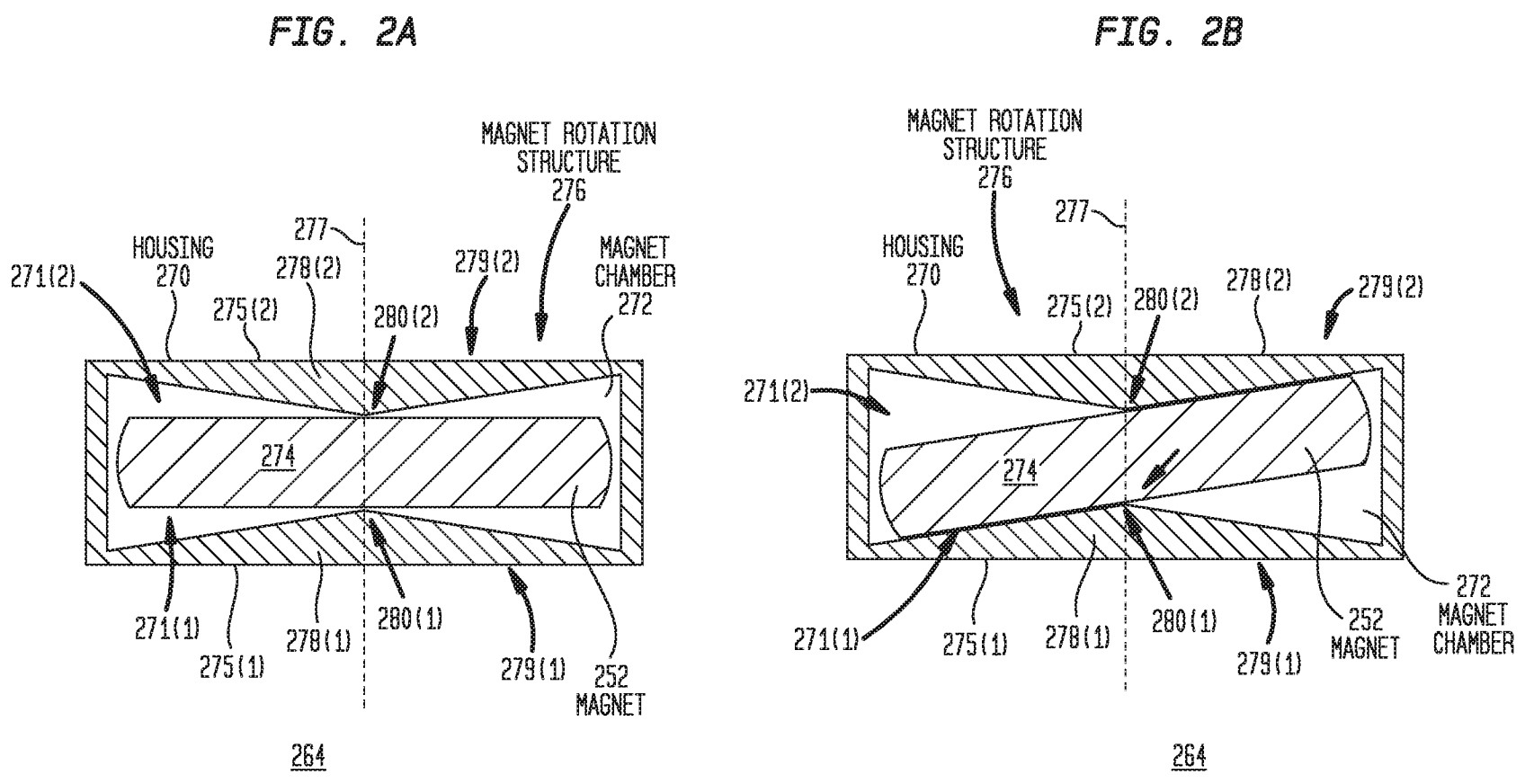

Referring first to FIGS. 2A and 2B, shown are cross-sectional views of an example housing arrangement 264 and a magnet 252. FIG. 2A illustrates a default arrangement of the magnet 252 within the housing arrangement 264 when the magnet 252 is exposed to a "system magnetic field" (e.g., a magnetic field present during normal use with a magnet positioned in an external component of the medical device system). FIG. 2B illustrates an out-of-plane rotated arrangement of the magnet 252 in the housing arrangement 264 when the magnet 252 is exposed to a misaligned external magnetic field (e.g., during an MRI).

In general, a misaligned external magnetic field can be applied during an MRI or other medical procedure. However, it is also noted that a misaligned external magnetic field could also be applied during normal use of the system. For example, the rotated arrangement shown in FIG. 2B could be acceptable during normal use if, for example, the external device magnet was canted due to a non-flat anatomy. Such an arrangement would not adversely affect performance of the device and positions between those shown in FIGS. 2A and 2B are also possible and acceptable. Therefore, as used herein, a misaligned external magnetic field is a magnetic field that would induce out-of-plane rotation of an implantable magnet, such as magnet 252. In certain embodiments, an external magnetic field is a "misaligned" external magnetic field when the external magnetic field is misaligned with the implantable magnet polarity by at least 0.5 degrees.

As shown, the housing arrangement 264 comprises a housing 270 defining a magnet chamber 272. In certain embodiments, the magnet 252 is referred to herein as a "planar" magnet because the magnet includes first and second substantially parallel surfaces, referred to as a first surface 271(1) and a second surface 271(2). The body 274 of the magnet 252 (e.g., the portion between the surfaces 271(1) and 271(2)) can have a variety of different shapes, such as a cylindrical shape, a rectangular shape, a barrel shape, etc. FIGS. 2A and 2B illustrates a specific example in which the body 274 of the magnet 252 has a barrel shape.

In the examples of FIGS. 2A and 2B, the magnet chamber 272 includes two walls/surfaces/sides 275(1) and 275(2) that are spaced from, but generally parallel to, the first and second surfaces 271(1) and 271(2), respectively, of the magnet 252. The housing arrangement 264 includes a magnet rotation structure 276 that is configured to permit both in-plane and out-of-plane rotation of the magnet 252. As used herein, "in-plane" rotation refers to rotation of the magnet 252 circumferentially around a central axis 277 of the body 274, while "out-of-plane" rotation refers to at least some angular rotation of the magnet 252 relative to central axis 277 (e.g., towards/away from the central axis 277).

In the embodiments shown in FIGS. 2A and 2B, the magnet rotation structure 276 comprises a first conical projection/member 278(1) and a second conical projection 278(2). The first conical projection 278(1) comprises a base 279(1) and an apex 280(1), while the second conical projection 278(2) comprises a base 279(2) and an apex 280(2). As shown, the first conical projection 278(1) extends from the first side 275(1) to the first magnet surface 271(1), where the apex 280(1) contacts the first magnet surface 271(1) adjacent/proximate to (e.g., at/along) the central axis 277. Also as shown, the second conical projection 278(2) extends from the second side 275(2) to the second magnet surface 271(2), where the apex 280(2) contacts the second magnet surface 271(2) adjacent/proximate to (e.g., at/along) the central axis 277. The first and second conical projections 278(1) and 278(2) can be integrated/unitary with the housing 270 or can be separate elements that are, for example, mechanically coupled to (e.g., adhered to, welded to, etc.) the housing.

In operation, when an external magnet is magnetically coupled to the magnet 252, the opposing conical projections 278(1) and 278(2) enable the magnet 252 to be arranged/oriented, as shown in FIG. 2A, for maximum mutual coupling. In certain embodiments, this orientation for maximum mutual coupling with an external magnet is substantially parallel to the surface/skin of the tissue under which the housing 270 is implanted. In addition, as shown in FIG. 2B, when a misaligned external magnetic field is applied, the opposing conical projections 278(1) and 278(2) enable the magnet 252 to rotate out-of-plane in order to be more closely aligned with the direction of the externally applied magnetic field, thereby reducing torque, and thus less pain and less risk of tissue or device damage, in the presence of the misaligned external magnetic field In summary, FIGS. 2A and 2B illustrate an embodiment in which the housing arrangement 264 includes a magnet rotation structure 276 formed by two opposing conical projections 278(1) and 278(2), where the apexes 280(1) and 280(2) of the conical projections 278(1) and 278(2) contact the magnet 252 adjacent to the central axis 277. This example magnet rotation structure 276 permits out-of-plane rotation of the magnet 252 in the presence of an externally applied magnet field, without a requirement for the magnet 252 to have any non-standard shape. That is, the example magnet rotation structure 276 operates with standard/traditional planar magnets.

FIGS. 3A and 3B are cross-sectional views of another example housing arrangement 364 and a magnet 352, in accordance with certain embodiments presented herein. FIG. 3A illustrates a default arrangement of the magnet 352 within the housing arrangement 364 when the magnet 352 is not exposed to an externally applied magnetic field (e.g., during normal use, such as when coupled to an external magnet). FIG. 3B illustrates an out-of-plane rotated arrangement of the magnet 352 in the housing arrangement 364 when the magnet 352 is exposed to an externally applied magnetic field (e.g., during an MRI).

As shown, the housing arrangement 364 comprises a housing 370 defining a magnet chamber 372. In certain embodiments, the magnet 352 is referred to herein as a "planar" magnet because the magnet includes first and second substantially parallel surfaces, referred to as a first surface 371(1) and a second surface 371(2). The body 374 of the magnet 352 (e.g., the portion between the surfaces 371(1) and 371(2)) can have a variety of different shapes, such as a cylindrical shape, a rectangular shape, a barrel shape, etc. FIGS. 3A and 3B illustrates a specific example in which the body 374 of the magnet 352 has a barrel shape.

In the examples of FIGS. 3A and 3B, the magnet chamber 372 includes two walls/surfaces/sides 375(1) and 375(2) that are spaced from, but generally parallel to, the first and second surfaces 371(1) and 371(2), respectively, of the magnet 352. The housing arrangement 364 includes a magnet rotation structure 376 that is configured to permit both in-plane (rotation of body 374 around central axis 377) and out-of-plane rotation (angular rotation of body 374 relative to the central axis 377) of the magnet 352.

In the embodiments shown in FIGS. 3A and 3B, the magnet rotation structure 376 comprises a rounded projection/member 378(1) (e.g., a mound or bump) and a second rounded projection 378(2). The first rounded projection 378(1) comprises a base 379(1) and a curved apex 380(1), while the second rounded projection 378(2) comprises a base 379(2) and a curved apex 380(2). As shown, the first rounded projection 378(1) extends from the first side 375(1) to the first magnet surface 371(1), where the curved apex 380(1) contacts the first magnet surface 371(1) adjacent/proximate to (e.g., at/along) the central axis 377. Also as shown, the second rounded projection 378(2) extends from the second side 375(2) to the second magnet surface 371(2), where the curved apex 380(2) contacts the second magnet surface 371(2) adjacent/proximate to (e.g., at/along) the central axis 377. The first and second rounded projections 378(1) and 378(2) can be integrated/unitary with the housing 370 or can be separate elements that are, for example, mechanically coupled to (e.g., adhered to, welded to, etc.) the housing. The rounded projections 378(1) and 378(2) are generally rigid (non-deformable) elements.

In operation, when an external magnet is magnetically coupled to the magnet 352, the opposing rounded projections 378(1) and 378(2) enable the magnet 352 to be arranged/oriented, as shown in FIG. 3A, for maximum mutual coupling. In certain embodiments, this orientation for maximum mutual coupling with an external magnet is substantially parallel to the surface/skin of the tissue under which the housing 370 is implanted. In addition, as shown in FIG. 3B, when a misaligned external magnetic field is applied, the opposing rounded projections 378(1) and 378(2) enable the magnet 352 to rotate out-of-plane in order to be more closely aligned with the direction of the externally applied magnetic field, thereby reducing torque, and thus less pain and less risk of tissue or device damage, in the presence of the misaligned external magnetic field In summary, FIGS. 3A and 3B illustrate an embodiment in which the housing arrangement 364 includes a magnet rotation structure 376 formed by two opposing rounded projections 378(1) and 378(2), where the curved apexes 380(1) and 380(2) of the rounded projections 378(1) and 378(2) contact the magnet 352 adjacent to the central axis 377. This example magnet rotation structure 376 permits out-of-plane rotation of the magnet 352 in the presence of an externally applied magnet field, without a requirement for the magnet 352 to have any non-standard shape. That is, the example magnet rotation structure 376 operates with standard/traditional planar magnets.

Figure 4B:
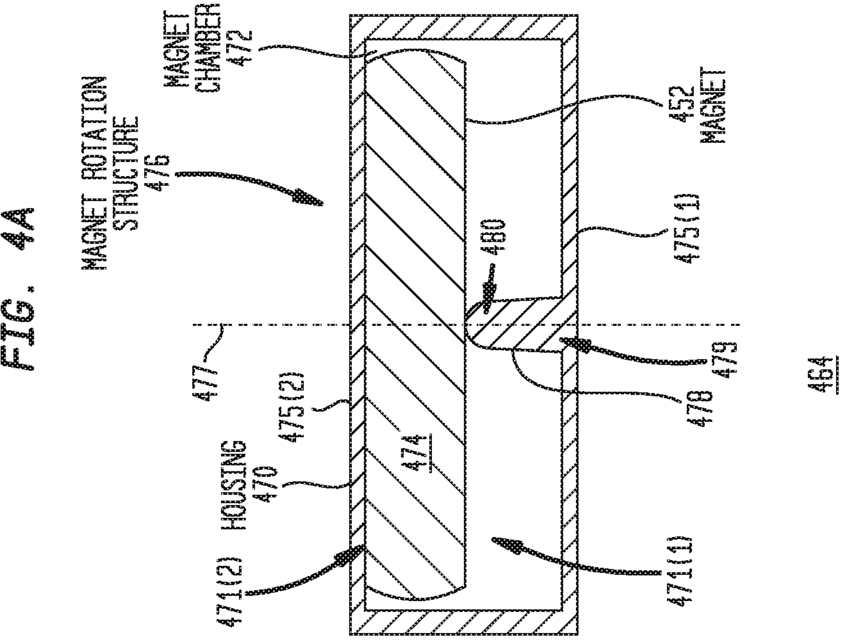

FIGS. 4A and 4B are cross-sectional views of another example housing arrangement 464 and a magnet 452, in accordance with certain embodiments presented herein. FIG. 4A illustrates a default arrangement of the magnet 452 within the housing arrangement 464 when the magnet 452 is not exposed to an externally applied magnetic field (e.g., during normal use, such as when coupled to an external magnet). FIG. 4B illustrates an out-of-plane rotated arrangement of the magnet 452 in the housing arrangement 464 when the magnet 452 is exposed to an externally applied magnetic field (e.g., during an MRI).

As shown, the housing arrangement 464 comprises a housing 470 defining a magnet chamber 472. In certain embodiments, the magnet 452 is referred to herein as a "planar" magnet because the magnet includes first and second substantially parallel surfaces, referred to as a first surface 471(1) and a second surface 471(2). The body 474 of the magnet 452 (e.g., the portion between the surfaces 471(1) and 471(2)) can have a variety of different shapes, such as a cylindrical/disc shape, modified disc shape, a rectangular shape, a barrel or pill shape, etc. FIGS. 4A and 4B illustrates a specific example in which the body 474 of the magnet 452 has a barrel shape.

In the examples of FIGS. 4A and 4B, the magnet chamber 472 includes two walls/surfaces/sides 475(1) and 475(2) that are spaced from, but generally parallel to, the first and second surfaces 471(1) and 471(2), respectively, of the magnet 452. The housing arrangement 464 includes a magnet rotation structure 476 that is configured to permit both in-plane (rotation of body 474 around central axis 477) and out-of-plane rotation (angular rotation of the body 474 relative to the central axis 477) of the magnet 452.

In the embodiments shown in FIGS. 4A and 4B, the magnet rotation structure 476 comprises a single deformable projection/member 478 (e.g., a mound or bump) extending from the first side of 475(1) of the magnet chamber 472. The deformable projection 478 is formed from a resiliently flexible (deformable) material (e.g., silicone rubber). As shown, the rounded projection 478 comprises a base 479 and a curved apex 480, where the curved apex 480 contacts the first magnet surface 471(1) adjacent/proximate to (e.g., at/along) the central axis 477. The deformable projection 478 can be integrated/unitary with the housing 470 or can be a separate element that is, for example, mechanically coupled to (e.g., adhered to, welded to, etc.) the housing.

In the examples of FIGS. 4A and 4B, the second side 475(2) of the magnet chamber 472 is configured to be positioned closest to the recipient's skin. As shown in FIG. 4A, in the default arrangement, the deformable projection 478 has sufficient rigidity to position the magnet 452 adjacent to the second side 475(2) of the magnet chamber 472. This positioning close to the second side 475(2) (and closest to the skin) can increase mutual coupling with an external magnet (e.g., the closer position increases magnet coupling). However, as shown in FIG. 4B, the rounded projection 478 is also configured to deform (e.g., bend) so as enable the magnet 452 to rotate out-of-plane in order to be more closely aligned with the direction of the externally applied magnetic field.

In operation, when an external magnet is magnetically coupled to the magnet 452, the deformable projection 478 enables the magnet 452 to be arranged/oriented, as shown in FIG. 4A, for maximum mutual coupling. In certain embodiments, this orientation for maximum mutual coupling with an external magnet is substantially parallel to the surface/skin of the tissue under which the housing 470 is implanted. In addition, as shown in FIG. 4B, when a misaligned external magnetic field is applied, the deformable projection 478 enables the magnet 452 to rotate out-of-plane in order to be more closely aligned with the direction of the externally applied magnetic field, thereby reducing torque, and thus less pain and less risk of tissue or device damage, in the presence of the misaligned external magnetic field In summary, FIGS. 4A and 4B illustrate an embodiment in which the housing arrangement 464 includes a magnet rotation structure 476 formed by a single deformable projection 478, where the curved apex 480 contacts the magnet 452 adjacent to the central axis 477. This example magnet rotation structure 476 permits out-of-plane rotation of the magnet 452 in the presence of an externally applied magnet field, without a requirement for the magnet 452 to have any non-standard shape. That is, the example magnet rotation structure 476 operates with standard/traditional planar magnets.

Figure 5A:
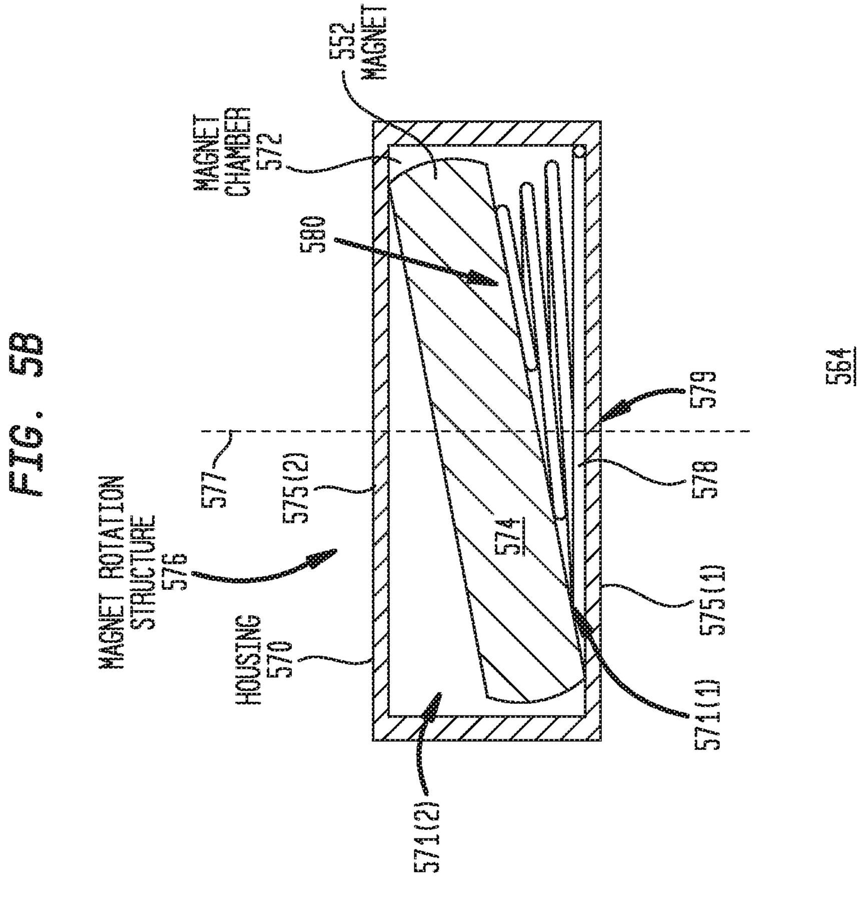

FIGS. 5A and 5B are cross-sectional views of another example housing arrangement 564 and a magnet 552, in accordance with certain embodiments presented herein. FIG. 5A illustrates a default arrangement of the magnet 552 within the housing arrangement 564 when the magnet 552 is not exposed to an externally applied magnetic field (e.g., during normal use, such as when coupled to an external magnet). FIG. 5B illustrates an out-of-plane rotated arrangement of the magnet 552 in the housing arrangement 564 when the magnet 552 is exposed to an externally applied magnetic field (e.g., during an MRI).

As shown, the housing arrangement 564 comprises a housing 570 defining a magnet chamber 572. In certain embodiments, the magnet 552 is referred to herein as a "planar" magnet because the magnet includes first and second substantially parallel surfaces, referred to as a first surface 571(1) and a second surface 571(2). The body 574 of the magnet 552 (e.g., the portion between the surfaces 571(1) and 571(2)) can have a variety of different shapes, such as a cylindrical shape, a rectangular shape, a barrel shape, etc. FIGS. 5A and 5B illustrates a specific example in which the body 574 of the magnet 552 has a barrel shape.

In the examples of FIGS. 5A and 5B, the magnet chamber 572 includes two walls/surfaces/sides 575(1) and 575(2) that are spaced from, but generally parallel to, the first and second surfaces 571(1) and 571(2), respectively, of the magnet 552. The housing arrangement 564 includes a magnet rotation structure 576 that is configured to permit both in-plane (rotation of body 574 around central axis 577) and out-of-plane rotation (angular rotation of the body 574 relative to the central axis 577) of the magnet 552.

Figure 5C:
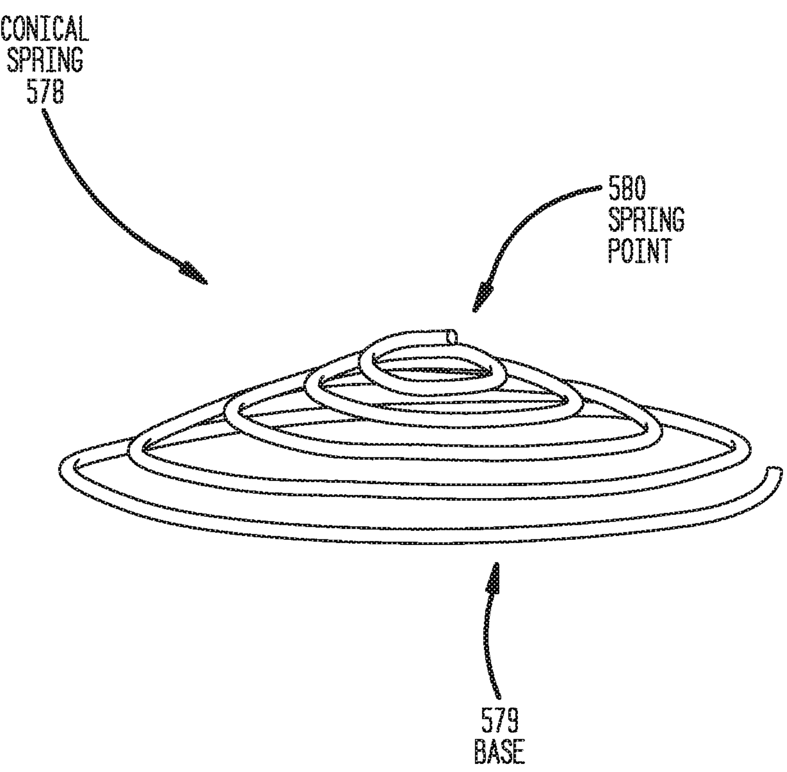
FIG. 5C is side-view of a conical spring used in the housing arrangement of FIGS. 5A and 5B.

In the embodiments shown in FIGS. 5A and 5B, the magnet rotation structure 576 comprises a single conical spring 578 extending from the first side of 575(1) of the magnet chamber 572. As shown, the conical spring 578 comprises a base 579 and a spring apex 580, where the spring apex 580 contacts the first magnet surface 571(1) adjacent/proximate to (e.g., at/along) the central axis 577. The conical spring 578 can be a separate element that is, for example, mechanically coupled to (e.g., adhered to, welded to, etc.) the housing, or a separate element that is assembled into the housing. FIG. 5C is a side-view of the conical spring 578 shown separate from the housing 570 and magnet 552.

In the examples of FIGS. 5A and 5B, the second side 575(2) of the magnet chamber 572 is configured to be positioned closest to the recipient's skin. As shown in FIG. 5A, in the default arrangement, the conical spring 578 has sufficient rigidity to position the magnet 552 adjacent to the second side 575(2) of the magnet chamber 572. This positioning close to the second side 575(2) (and closest to the skin) can increase mutual coupling with an external magnet (e.g., the closer position increases magnet coupling). However, as shown in FIG. 5B, the conical spring 578 is also configured to deform (e.g., bend) so as enable the magnet 552 to rotate out-of-plane in order to be more closely aligned with the direction of the externally applied magnetic field.

In operation, when an external magnet is magnetically coupled to the magnet 552, the conical spring 578 enables the magnet 552 to be arranged/oriented, as shown in FIG. 5A, for maximum mutual coupling. In certain embodiments, this orientation for maximum mutual coupling with an external magnet is substantially parallel to the surface/skin of the tissue under which the housing 570 is implanted. In addition, as shown in FIG. 5B, when a misaligned external magnetic field is applied, the conical spring 578 enables the magnet 552 to rotate out-of-plane in order to be more closely aligned with the direction of the externally applied magnetic field, thereby reducing torque, and thus less pain and less risk of tissue or device damage, in the presence of the misaligned external magnetic field In summary, FIGS. 5A and 5B illustrate an embodiment in which the housing arrangement 564 includes a magnet rotation structure 576 formed by a single conical spring 578, where the spring apex 580 contacts the magnet 552 adjacent to the central axis 577. This example magnet rotation structure 576 permits out-of-plane rotation of the magnet 552 in the presence of an externally applied magnet field, without a requirement for the magnet 552 to have any non-standard shape. That is, the example magnet rotation structure 576 operates with standard/traditional planar magnets.

As noted, FIGS. 5A and 5B illustrate an embodiment in which the magnet rotation structure 576 comprises a single conical spring 578. In alternative embodiments, the net rotation structure 576 can comprise two opposing conical springs, where each spring extends from a corresponding one of the first side 575(1) and the second side 575(2).

FIGS. 2A-2B, 3A-3B, 4A-4B, and 5A-5C generally illustrate arrangements that include a single magnet. In accordance with alternative embodiments, the single magnet can be replaced with two or more magnets. FIGS. 6A-6C and 7A-7B illustrate example embodiments that include two magnets. For ease of description, the embodiments of FIGS. 6A-6C and 7A-7B will be described with reference to housing arrangement 264 and magnet rotation structure 276 from FIGS. 2A and 2B. For ease of description, the details of housing arrangement 264 are not repeated with reference to FIGS. 6A-6C and 7A-7B. It is to be appreciated that these examples are merely illustrative and that any of the embodiments of FIG. 3A-3B, 4A-4B, or 5A-5C could be implemented with multiple magnets, as shown in FIGS. 6A-6C and 7A-7B.

Figure 6B:
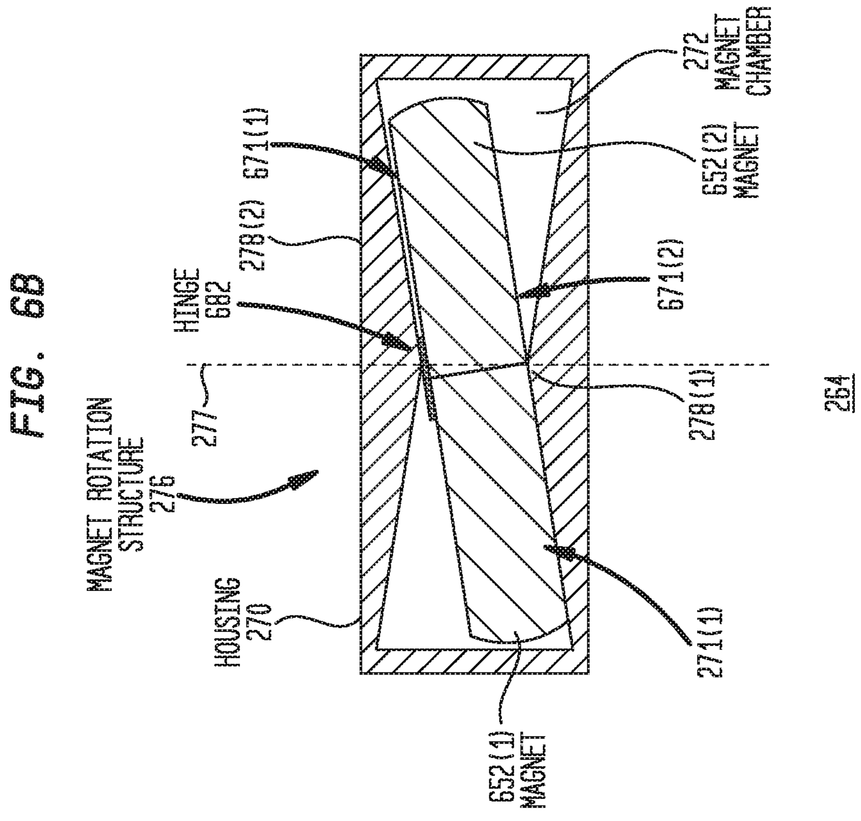
FIGS. 6A and 6B are cross-sectional views of a housing arrangement used with two magnets, in accordance with certain embodiments presented herein.
Figure 6A:
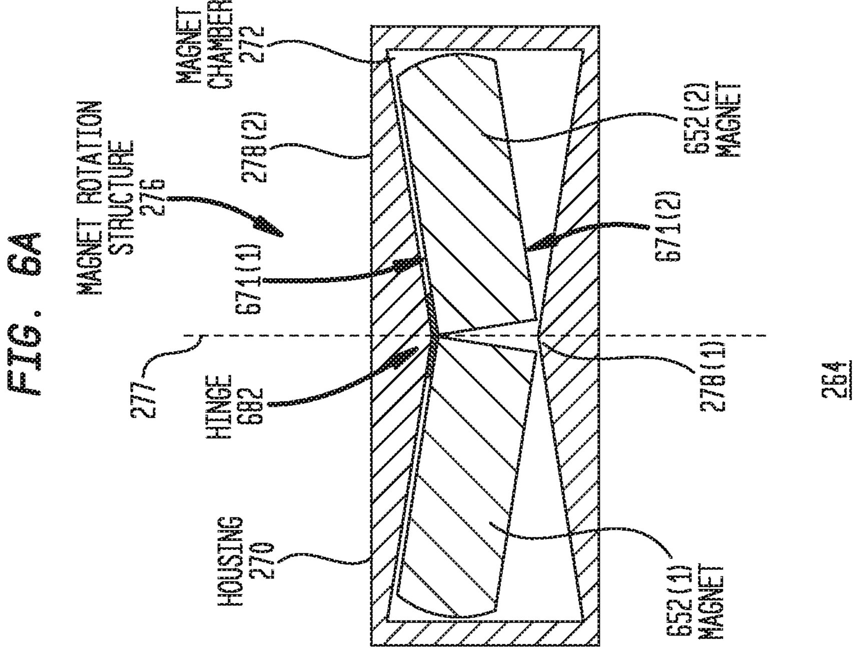

Referring first to FIGS. 6A and 6B, shown are cross-sectional views of the magnet rotation structure 276 having the opposing conical projections 278(1) and 278(2), where two magnets 652(1) and 652(2) are located between the conical projections. FIG. 6A illustrates a default arrangement of the two magnets 652(1) and 652(2) within the housing arrangement 264 when the two magnets 652(1) and 652(2) are not exposed to an externally applied magnetic field (e.g., during normal use, such as when coupled to one or more external magnets). FIG. 6B illustrates an out-of-plane rotated arrangement of the two magnets 652(1) and 652(2) in the housing arrangement 264 when the two magnets 652(1) and 652(2) are exposed to an externally applied magnetic field (e.g., during an MRI).

Figure 6C:
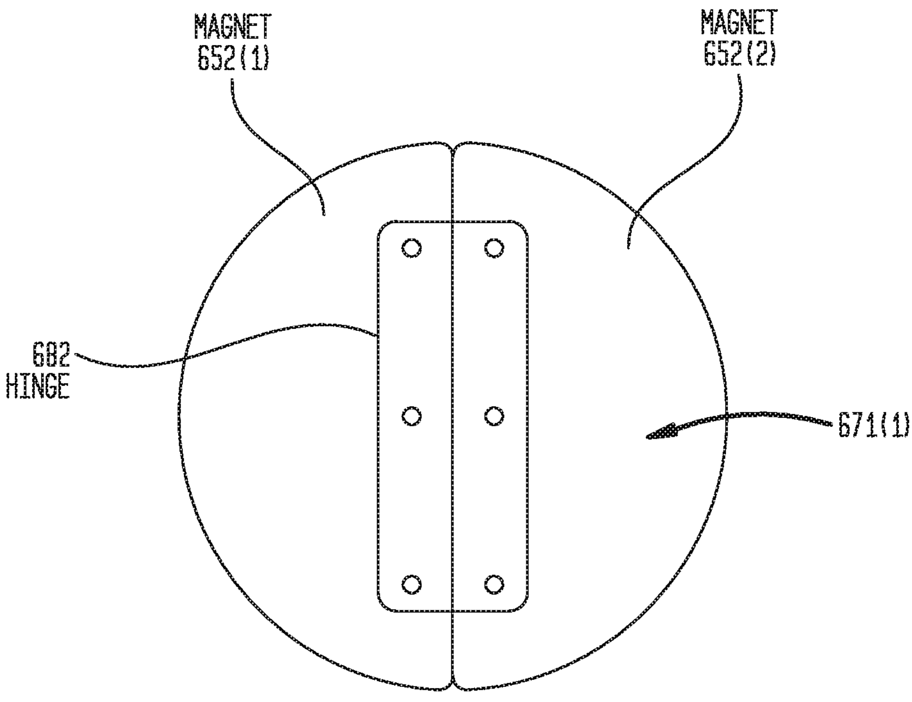
FIG. 6C is top-view of the two magnets of FIGS. 6A and 6B.

As shown, in the examples of FIGS. 6A and 6B, the magnets 652(1) and 652(2) are mechanically coupled via at least one hinge 682. The hinge 682 is, for example, a double action mechanical hinge, a portion of resiliently flexible material (soft polymer hinge), or other mechanism that is attached to both magnets and permits bi-directional angular rotation of each of magnet 652(1) and 652(2) (e.g., angular rotation relative to axis 277). FIG. 6C is a top-view of the hinge 682 and the magnets 652(1) and 652(2)

Figure 7B:
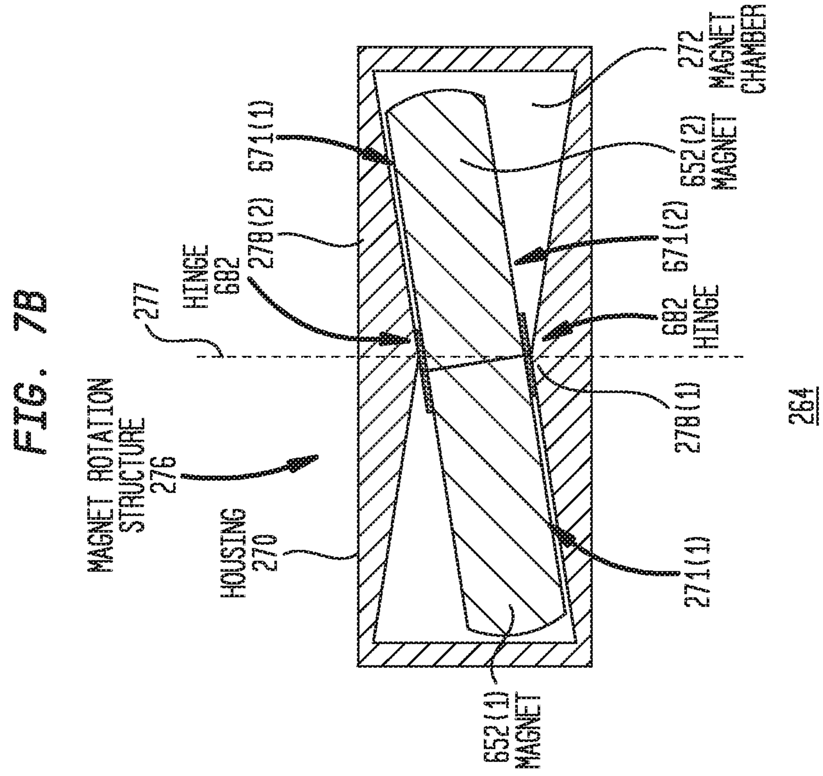
FIGS. 7A and 7B are cross-sectional views of a housing arrangement used with two magnets, in accordance with certain embodiments presented herein.
Figure 7A:
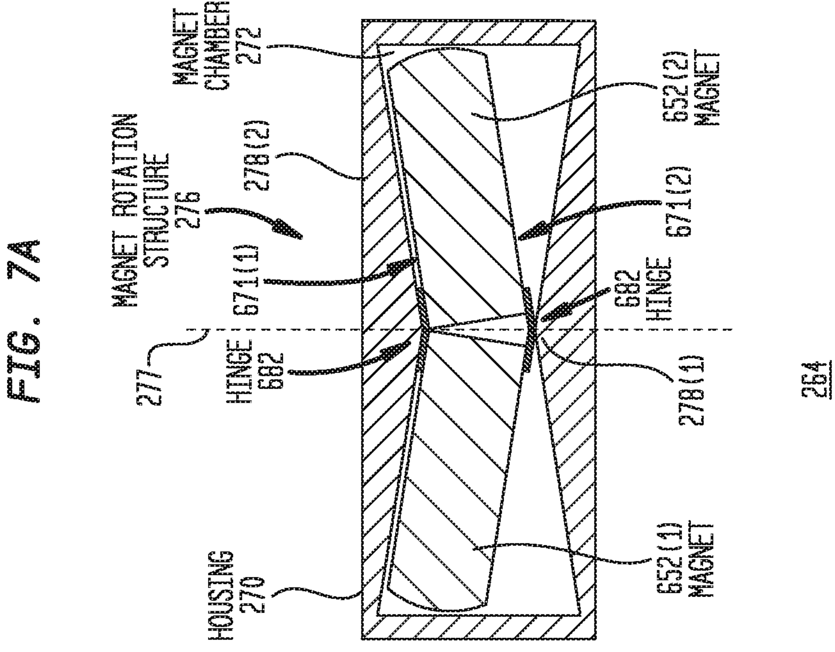

In certain examples, the magnets 652(1) and 652(2) are used in a four-pole magnet arrangement where magnets 652(1) and 652(2) are two magnet "halves" with opposite polarization. As such, in the operational/default arrangement of FIG. 6A, two external magnet halves (not shown in FIGS. 6A/6B), each having the correct polarity for coupling to a corresponding one of the magnets 652(1) and 652(2), would be magnetically coupled to the magnets 652(1) and 652(2). The opposing conical projections 278(1) and 278(2) and the hinge 682 enable the magnets 652(1) and 652(2) to be arranged/oriented, as shown in FIG. 6A, for maximum mutual coupling with the external magnets. In addition, as shown in FIG. 6B, when a misaligned external magnetic field is applied, the opposing conical projections 278(1) and 278(2) and the hinge 682 enable one or both of the magnets 652(1) and 652(2) to rotate out-of-plane in order to be more closely aligned with the direction of the externally applied magnetic field, thereby reducing torque, and thus less pain and less risk of tissue or device damage, in the presence of the misaligned external magnetic field FIGS. 6A-6C illustrate an embodiment in which a single hinge 682 is used to mechanically couple the magnets 652(1) and 652(2) together at a first surface 671(1) of the magnets. It is to be appreciated that, as shown in FIGS. 7A and 7B, a second hinge 682 can also be provided at a second surface 671(2) of the magnets 652(1) and 652(2) such that the magnets 652(1) and 652(2) have two points of coupling.

FIGS. 8A-8C and 9A-9B illustrate example embodiments that include three magnets. For ease of description, the embodiments of FIGS. 8A-8C and 8A-8B will be described with reference to a housing arrangement 864 and magnet rotation structure 876. For ease of description, the details of housing arrangement 864 are described with reference to FIGS. 8A-8C.

Figures 8A, 8B:
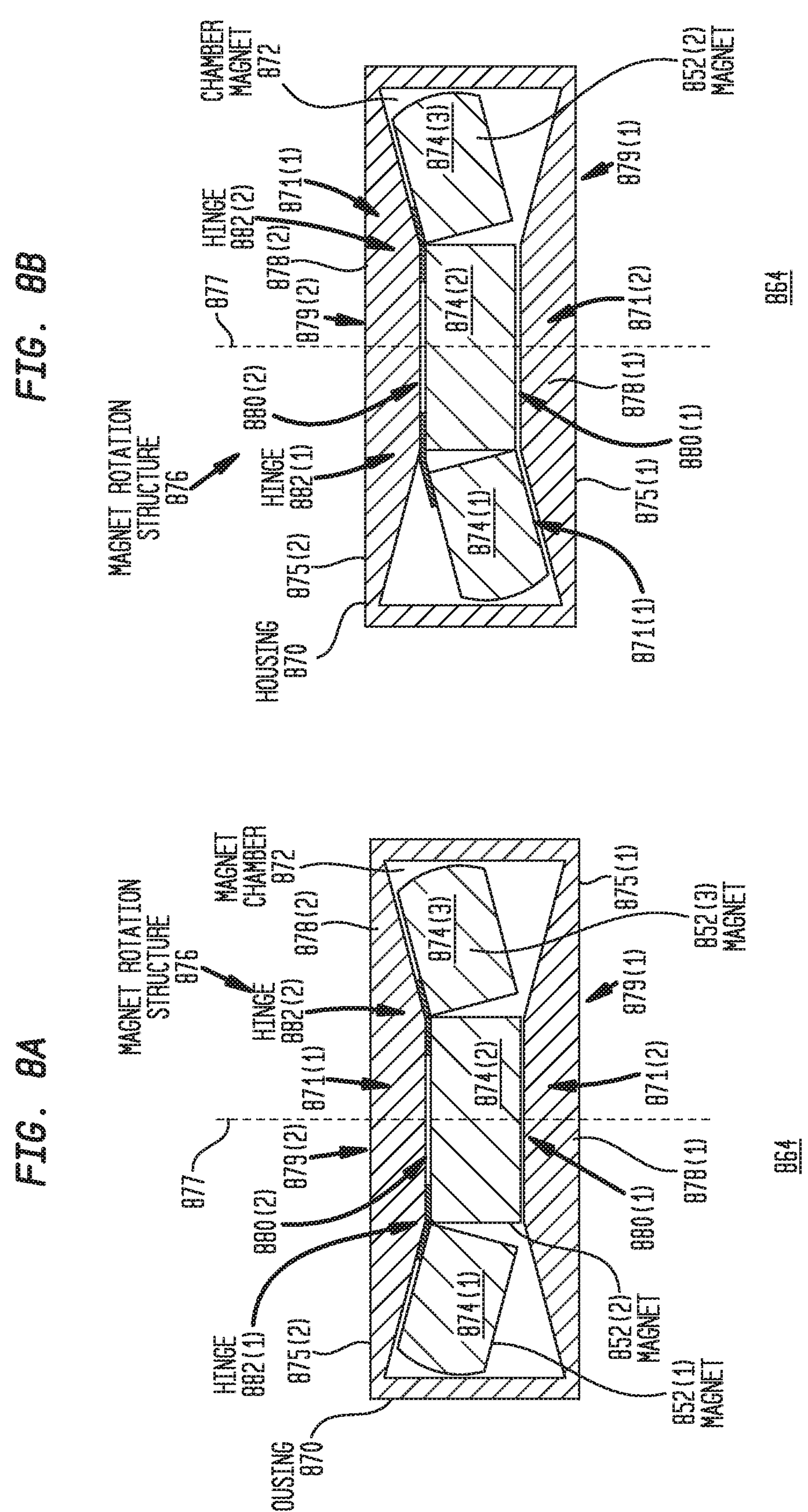
FIGS. 8A and 8B are cross-sectional views of a housing arrangement used with three magnets, in accordance with certain embodiments presented herein.

FIGS. 8A and 8B are cross-sectional views of an example housing arrangement 864 and three magnets, referred to as magnets 852(1), 852(2), and 852(3). FIG. 8A illustrates a default arrangement of the magnets 852(1), 852(2), and 852(3) within the housing arrangement 864 when the magnets 852(1), 852(2), and 852(3) are not exposed to an externally applied magnetic field (e.g., during normal use, such as when coupled to an external magnet). FIG. 8B illustrates an out-of-plane rotated arrangement of the magnets 852(1), 852(2), and 852(3) in the housing arrangement 864 when the magnets 852(1), 852(2), and 852(3) are exposed to an externally applied magnetic field (e.g., during an MRI).

As shown, the housing arrangement 864 comprises a housing 870 defining a magnet chamber 872. In certain embodiments, the magnets 852(1), 852(2), and 852(3) are referred to herein as a "planar" magnet because the magnets includes first and second substantially parallel surfaces, referred to as a first surface 871(1) and a second surface 871(2). The bodies 874(1), 874(2), and 874(3) of the magnets 852(1), 852(2), and 852(3) (e.g., the portion between the surfaces 871(1) and 871(2)) can have a variety of different shapes, such as a cylindrical shape, a rectangular shape, a barrel shape, etc.

In the examples of FIGS. 8A and 8B, the magnet chamber 872 includes two walls/surfaces/sides 875(1) and 875(2) that are spaced from, but generally parallel to, the first and second surfaces 871(1) and 871(2), respectively, of the magnets 852(1), 852(2), and 852(3). The housing arrangement 864 includes a magnet rotation structure 876 that is configured to permit both in-plane and out-of-plane rotation of one or more of the magnets 852(1), 852(2), and 852(3). As used herein, "in-plane" rotation refers to rotation of one or more of the magnets 852(1), 852(2), and 852(3) circumferentially around a central axis 877, while "out-of-plane" rotation refers to at least some angular rotation of one or more of the magnets 852(1), 852(2), and 852(3) relative to the central axis 877 (e.g., at least some movement towards/away from the central axis 877).

In the embodiments shown in FIGS. 8A and 8B, the magnet rotation structure 876 comprises a first frustoconical projection/member 878(1) and a second frustoconical projection 878(2). As shown, the first frustoconical projection 878(1), which comprises a base 879(1) and a flat apex 880(1), extends from the first side 875(1) to the first magnet surface 871(1) of the magnet 852(2). The first frustoconical projection 878(1) contacts the magnet 852(2) adjacent/proximate to (e.g., at/along) the central axis 877. Also as shown, the second frustoconical projection 878(2), which comprises a base 879(2) and a flat apex 880(2), extends from the second side 875(2) to the second magnet surface 871(2). The second frustoconical projection 878(2) contacts the magnet 852(2) adjacent/proximate to (e.g., at/along) the central axis 877. The first and second frustoconical projections 878(1) and 878(2) can be integrated/unitary with the housing 870 or can be separate elements that are, for example, mechanically coupled to (e.g., adhered to, welded to, etc.) the housing.

Figure 8C:
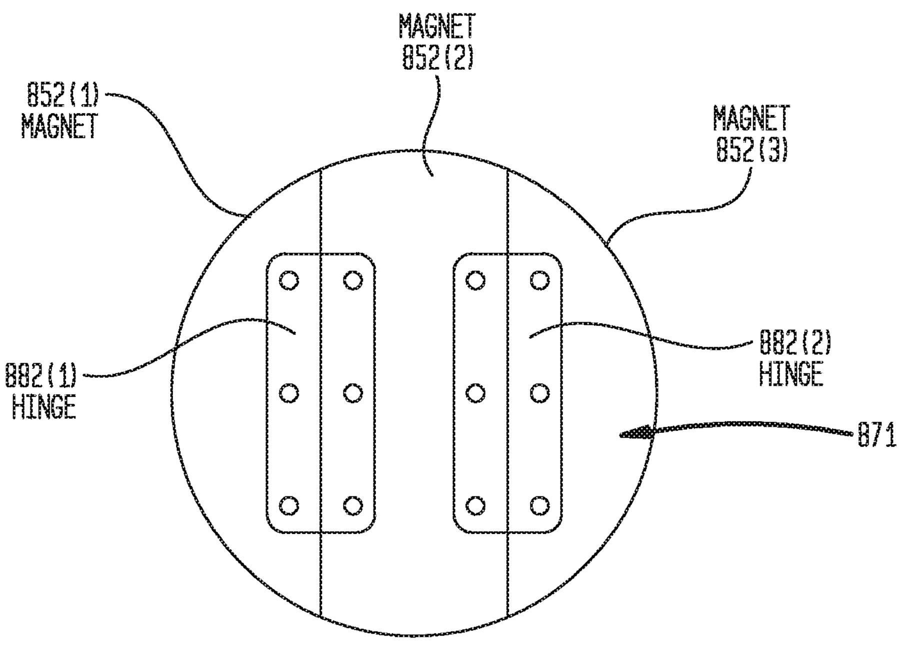
FIG. 8C is top-view of the three magnets of FIGS. 8A and 8B.

As shown, in the examples of FIGS. 8A and 8B, the magnets 852(1), 852(2), and 852(3) are mechanically coupled via at least two hinges 882(1) and 882(2). More specifically hinge 882(1) couples the magnet 852(1) to magnet 852(2), while hinge 882(2) couples the magnet 852(2) to hinge 852(2), on the opposing side from magnet 852(1.) The hinges 882(1) and 882(2) are, for example, double action mechanical hinges, portions of resiliently flexible material (soft polymer hinges), or other mechanisms that are attached to the magnets and permit bi-directional angular rotation of each of magnet 852(1) and 852(3) (e.g., angular rotation relative to axis 877). FIG. 8C is a top-view of the hinges 882(1) and 882(2) and the magnets 852(1), 852(2), and 852(3).

In certain examples, the magnets 852(1) and 852(3) are used in a halbach array where magnets 852(1) and 852(3) are two magnet "halves" with opposite polarization, while magnet 852(2) is polarized in plane. In the operational/default arrangement of FIG. 8A, the halbach array of FIGS. 8A-8C can couple to an external diametric, four pole, or another halbach external magnet array.

Figure 9B:
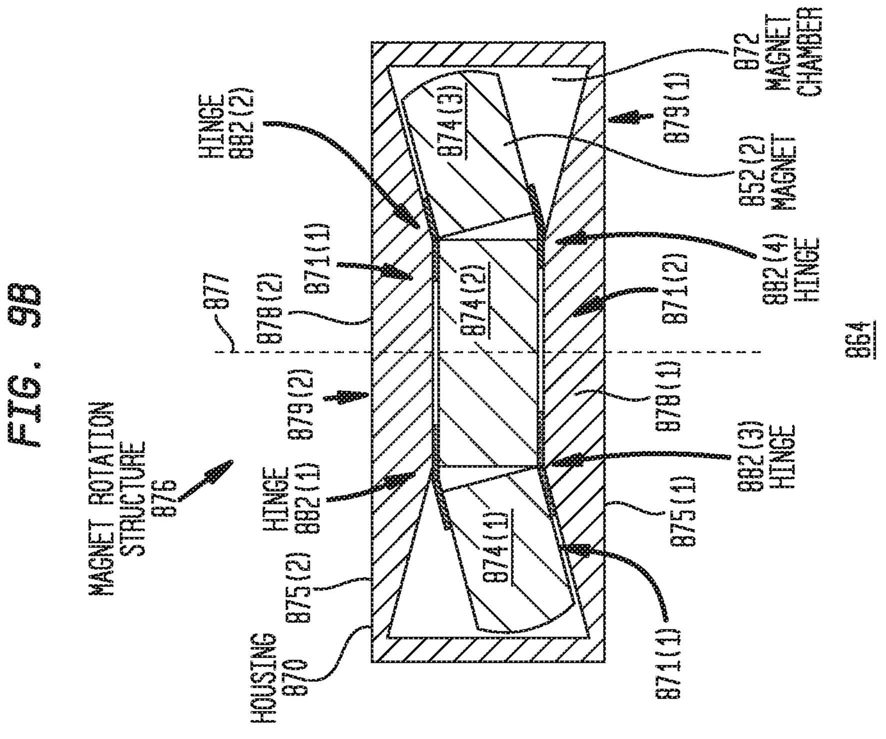
FIGS. 9A and 9B are cross-sectional views of a housing arrangement used with three magnets, in accordance with certain embodiments presented herein.
Figure 9A:
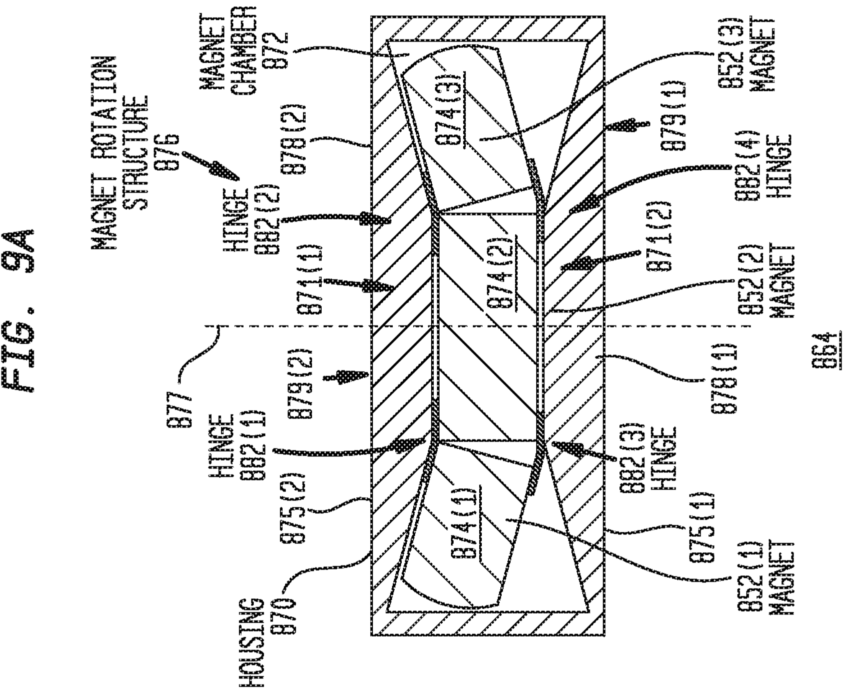

The opposing frustoconical projections 878(1) and 878(2) and the hinges 882(1) and 882(2) enable the magnets 852(1) and 852(3) to be arranged/oriented, as shown in FIG. 8A, for maximum mutual coupling with the external magnets. In addition, as shown in FIG. 8B, when a misaligned external magnetic field is applied, the frustoconical projections 878(1) and 878(2) and the hinges 882(1) and 882(2) enable one or both of the magnets 852(1) and 852(3) to rotate out-of-plane in order to be more closely aligned with the direction of the externally applied magnetic field, thereby reducing torque, and thus less pain and less risk of tissue or device damage, in the presence of the misaligned external magnetic field FIGS. 8A-8C illustrate an embodiment in which a two hinges 882(1) and 882(2) are used to mechanically couple the magnets 852(1) and 852(3) with magnet 852(2) at a first surface 871(1) of the magnets. It is to be appreciated that, as shown in FIGS. 9A and 9B, a third and fourth hinges 882(3) and 882(4) can also be provided at a second surface 871(2) of the magnets such that the magnets 852(1) and 852(3) each have two points of coupling with magnet 852(2).

Figure 10:
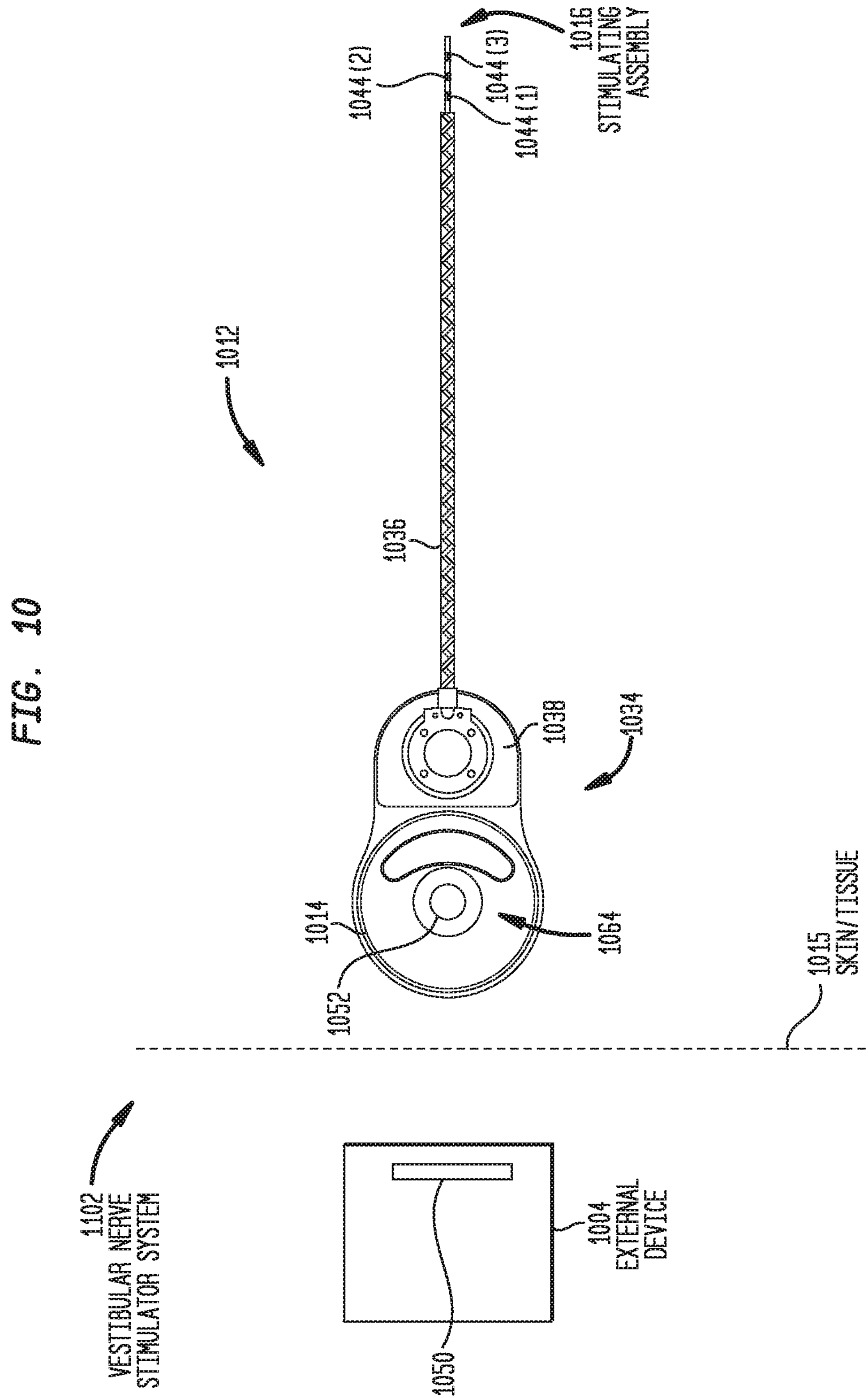
FIG. 10 illustrates an example vestibular stimulator system, in accordance with certain embodiments presented herein.

FIG. 10 illustrates an example vestibular stimulator system 1002, with which embodiments presented herein can be implemented. As shown, the vestibular stimulator system 1002 comprises an implantable component (vestibular stimulator) 1012 and an external device/component 1004 (e.g., external processing device, battery charger, remote control, etc.). The external device 1004 comprises an external magnet 1050 and is configured to transfer data (and potentially power) to the vestibular stimulator 1012, The vestibular stimulator 1012 comprises an implant body (main module) 1034, a lead region 1036, and a stimulating assembly 1016, all configured to be implanted under the skin/tissue (tissue) 1015 of the recipient. The implant body 1034 generally comprises a hermetically-sealed housing 1038 in which RF interface circuitry, one or more rechargeable batteries, one or more processors, and a stimulator unit are disposed. The implant body 134 also includes an internal/implantable coil 1014 that is generally external to the housing 1038, but which is connected to the transceiver via a hermetic feedthrough (not shown). Moreover, the implant body 134 includes a housing arrangement 1064, as described elsewhere herein, with a magnet 1052 retained therein.

The stimulating assembly 1016 comprises a plurality of electrodes 1044 disposed in a carrier member (e.g., a flexible silicone body). In this specific example, the stimulating assembly 1016 comprises three (3) stimulation electrodes, referred to as stimulation electrodes 1044(1), 1044(2), and 1044(3). The stimulation electrodes 1044(1), 1044(2), and

1044(3) function as an electrical interface for delivery of electrical stimulation signals to the recipient's vestibular system.

The stimulating assembly 1016 is configured such that a surgeon can implant the stimulating assembly adjacent the recipient's otolith organs via, for example, the recipient's oval window. It is to be appreciated that this specific embodiment with three stimulation electrodes is merely illustrative and that the techniques presented herein may be used with stimulating assemblies having different numbers of stimulation electrodes, stimulating assemblies having different lengths, etc.

In operation, the vestibular stimulator 1012, the external device 1004, and/or another external device, can be configured to implement the techniques presented herein. That is, the vestibular stimulator 1012, possibly in combination with the external device 1004 and/or another external device, can include an evoked biological response analysis system, as described elsewhere herein.

As should be appreciated, while particular uses of the technology have been illustrated and discussed above, the disclosed technology can be used with a variety of devices in accordance with many examples of the technology. The above discussion is not meant to suggest that the disclosed technology is only suitable for implementation within systems akin to that illustrated in the figures. In general, additional configurations can be used to practice the processes and systems herein and/or some aspects described can be excluded without departing from the processes and systems disclosed herein.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., portions, components, etc.) described with respect to the figures herein are not intended to limit the systems and processes to the particular aspects described. Accordingly, additional configurations can be used to practice the methods and systems herein and/or some aspects described can be excluded without departing from the methods and systems disclosed herein.

Similarly, where steps of a process are disclosed, those steps are described for purposes of illustrating the present methods and systems and are not intended to limit the disclosure to a particular sequence of steps. For example, the steps can be performed in differing order, two or more steps can be performed concurrently, additional steps can be performed, and disclosed steps can be excluded without departing from the present disclosure. Further, the disclosed processes can be repeated.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

It is also to be appreciated that the embodiments presented herein are not mutually exclusive and that the various embodiments may be combined with another in any of a number of different manners.

What is claimed is:

1. An implantable medical device, comprising:

an implantable housing defining a magnet chamber comprising a first side and a second side disposed opposite to the first side;

at least one magnet disposed in the magnet chamber between the first side and the second side, wherein the at least one magnet comprises a first magnet surface adjacent the first side and a second magnet surface adjacent the second side; and a magnet rotation structure extending from at least the first side to the first magnet surface, wherein the magnet rotation structure is arranged for out-of-plane rotation of the at least one magnet in the presence of a misaligned external magnetic field.

2. The implantable medical device of claim 1, wherein the magnet rotation structure comprises a first projection extending from the first side to the first magnet surface, and a second projection extending from the second side to the second magnet surface.

3. The implantable medical device of claim 2, wherein the first projection and the second projection each have a conical shape.

4. The implantable medical device of claim 2, wherein the first projection and the second projection each have a frustoconical shape.

5. The implantable medical device of claim 2, wherein the first projection and the second projection each comprises a rigid rounded projection.

6. The implantable medical device of claim 1, wherein the magnet rotation structure comprises a conical spring extending from the first side to the first magnet surface.

7. The implantable medical device of claim 1, wherein the magnet rotation structure comprises a first conical spring extending from the first side to the first magnet surface, and a second conical spring extending from the second side to the second magnet surface.

8. The implantable medical device of claim 1, wherein the magnet rotation structure comprises a first resiliently flexible projection extending from the first side to the first magnet surface.

9. The implantable medical device of claim 8, where, in the absence of an externally applied magnetic field, the first resiliently flexible projection is configured to retain the magnet in a default position abutting the second side.

10. The implantable medical device of claim 1, wherein the at least one magnet comprises a first magnet and a second magnet, and wherein the implantable medical device further comprises:

at least one hinge mechanically coupling the first magnet to the second magnet, wherein the at least one hinge is configured for bi-directional angular rotation of the first magnet and the second magnet relative to one another.

11. The implantable medical device of claim 10, wherein the at least one hinge comprises a double action mechanical hinge.

12. The implantable medical device of claim 10, wherein the at least one hinge comprises a soft polymer hinge.

13. The implantable medical device of claim 10, wherein the at least one hinge comprises a first hinge disposed at the first magnet surface and a second hinge disposed at the second magnet surface.

14. The implantable medical device of claim 1, wherein the at least one magnet comprises a first magnet, a second magnet, and a third magnet, wherein the implantable medical device further comprises:

at least one first hinge mechanically coupling the first magnet to the second magnet, and at least one second hinge mechanically coupling the third magnet to the second magnet, wherein the at least one first hinge is configured for bi-directional angular rotation of the first magnet relative to the second magnet, and wherein the at least one second hinge is configured for bi-directional angular rotation of the third magnet relative to the second magnet.

15. The implantable medical device of claim 14, wherein the at least one first hinge comprises a first hinge disposed at the first magnet surface and a third hinge disposed at the second magnet surface, and wherein at least one second hinge comprises a second hinge disposed at the first magnet surface and a fourth hinge disposed at the second magnet surface.

16. The implantable medical device of claim 1, wherein the at least one magnet has a barrel shape.

17. The implantable medical device of claim 1, wherein the misaligned external magnetic field is misaligned with a polarity of the at least one magnet by at least 0.5 degrees.

18. An apparatus, comprising:

a housing defining a magnet chamber;

a magnet arrangement comprising at least a first planar magnet; and a magnet rotation structure disposed in the magnet chamber, wherein the magnet rotation structure is separate from the magnet arrangement, and wherein the magnet rotation structure is configured to permit out-of-plane rotation of the at least first planar magnet in the presence of a misaligned external magnetic field.

19. The apparatus of claim 18, wherein the magnet rotation structure is integrated with the housing.

20. The apparatus of claim 18, wherein the magnet rotation structure comprises first and second projections extending from opposing sides of the magnet chamber.

21. The apparatus of claim 20, wherein the first and second projections each have at least one of a conical or frustoconical shape.

22. The apparatus of claim 20, wherein the first and second projections each comprise a rigid rounded projection.

23. The apparatus of claim 18, wherein the magnet rotation structure comprises a conical spring extending from a first side of the magnet chamber.

24. The apparatus of claim 23, wherein the magnet rotation structure further comprises a second conical spring extending from a second side of the magnet chamber.

25. The apparatus of claim 18, wherein the magnet rotation structure comprises a first resiliently flexible projection extending from a first side of the magnet chamber.

26. The apparatus of claim 25, where, in the absence of an externally applied magnetic field, the first resiliently flexible projection is configured to retain the at least first planar magnet in a default position abutting a second side of the magnet chamber.

27. The apparatus of claim 18, wherein the magnet arrangement comprises the at least first planar magnet and a second planar magnet, and wherein apparatus further comprises:

at least one hinge mechanically coupling the at least first planar magnet to the second planar magnet, wherein the at least one hinge is configured for bi-directional angular rotation of the at least first planar magnet and the second planar magnet relative to one another.

28. The apparatus of claim 27, wherein the magnet arrangement comprises the at least first planar magnet, a second planar magnet, and a third planar magnet, wherein the apparatus further comprises:

at least one first hinge mechanically coupling the at least first planar magnet to the second planar magnet, and at least one second hinge mechanically coupling the third planar magnet to the second planar magnet, wherein the at least one first hinge is configured for bi-directional angular rotation of the at least first planar magnet relative to the second planar magnet, and wherein the at least one second hinge is configured for bi-directional angular rotation of the third planar magnet relative to the second planar magnet.

29. The apparatus of claim 28, wherein the at least one first hinge comprises a first hinge disposed at a first surface of the magnet arrangement and a third hinge disposed at a second surface of the magnet arrangement, and wherein at least one second hinge comprises a second hinge disposed at the first surface of the magnet arrangement and a fourth hinge disposed at the second surface of the magnet arrangement.

* * * * *